US 12,257,296 B2
(12) United States Patent
Moore et al.

(10) Patent No.: US 12,257,296 B2
(45) Date of Patent: *Mar. 25, 2025

(54) CHIMERIC RSV, IMMUNOGENIC COMPOSITIONS, AND METHODS OF USE

(71) Applicant: EMORY UNIVERSITY, Atlanta, GA (US)

(72) Inventors: Martin L. Moore, Decatur, GA (US); Christina Rostad, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/575,829

(22) Filed: Jan. 14, 2022

(65) Prior Publication Data

US 2023/0293660 A1 Sep. 21, 2023

Related U.S. Application Data

(63) Continuation of application No. 15/772,275, filed as application No. PCT/US2016/058976 on Oct. 27, 2016, now Pat. No. 11,235,050.

(60) Provisional application No. 62/334,547, filed on May 11, 2016, provisional application No. 62/247,962, filed on Oct. 29, 2015.

(51) Int. Cl.
| A61K 39/12 | (2006.01) |
| C07K 14/005 | (2006.01) |
| C12N 7/00 | (2006.01) |
| A61K 39/00 | (2006.01) |
| A61P 11/00 | (2006.01) |

(52) U.S. Cl.
CPC ............ *A61K 39/12* (2013.01); *C07K 14/005* (2013.01); *C12N 7/00* (2013.01); *A61K 2039/5254* (2013.01); *A61P 11/00* (2018.01); *C12N 2760/18521* (2013.01); *C12N 2760/18534* (2013.01); *C12N 2760/18562* (2013.01)

(58) Field of Classification Search
None
See application file for complete search history.

(56) References Cited

U.S. PATENT DOCUMENTS

| 5,618,682 | A | 4/1997 | Scheirer |
| 5,674,713 | A | 10/1997 | Mcelroy et al. |
| 5,922,326 | A | 7/1999 | Murphy et al. |
| 5,976,796 | A | 11/1999 | Szalay et al. |
| 5,993,824 | A | 11/1999 | Murphy et al. |
| 6,033,886 | A | 3/2000 | Conzelmann |
| 6,074,859 | A | 6/2000 | Hirokawa et al. |
| 6,214,805 | B1 | 4/2001 | Torrence et al. |
| 6,264,957 | B1 | 7/2001 | Collins |
| 6,689,367 | B1 | 2/2004 | Collins et al. |
| 6,699,476 | B1 | 3/2004 | Collins et al. |
| 6,713,066 | B1 | 3/2004 | Collins et al. |
| 6,790,449 | B2 | 9/2004 | Collins |
| 6,923,971 | B2 | 8/2005 | Krempl et al. |
| 7,465,574 | B2 | 12/2008 | Jin et al. |
| 7,485,440 | B2 | 2/2009 | Collins et al. |
| 7,572,904 | B2 | 8/2009 | Cheng et al. |
| 7,744,902 | B2 | 6/2010 | Krempl et al. |
| 7,846,455 | B2 | 12/2010 | Collins et al. |
| 7,951,384 | B2 | 5/2011 | Morrison et al. |
| 8,163,530 | B2 | 4/2012 | Cheng et al. |
| 8,580,270 | B2 | 11/2013 | Morrison |
| 8,772,256 | B2 | 7/2014 | Graham |
| 8,846,051 | B2 | 9/2014 | Kew et al. |
| 9,011,876 | B2 | 4/2015 | Yagodich et al. |
| 9,107,939 | B2 | 8/2015 | Luytjes et al. |
| 9,476,032 | B2 | 10/2016 | Wimmer et al. |
| 9,492,525 | B2 | 11/2016 | Fattom et al. |
| 9,624,375 | B2 | 4/2017 | Wonneberger et al. |
| 10,232,032 | B2 | 3/2019 | Moore et al. |
| 10,792,356 | B2 | 10/2020 | Moore et al. |
| 11,471,524 | B2 | 10/2022 | Moore et al. |
| 2008/0118530 | A1 | 5/2008 | Kew et al. |
| 2009/0285853 | A1 | 11/2009 | Cheng et al. |
| 2011/0097358 | A1 | 4/2011 | Galarza et al. |
| 2012/0264217 | A1 | 10/2012 | Moore et al. |
| 2014/0271699 | A1 | 9/2014 | Kwong |
| 2014/0356390 | A1 | 12/2014 | Kew et al. |
| 2015/0368622 | A1 | 12/2015 | Collins et al. |
| 2016/0030549 | A1 | 2/2016 | Moore et al. |
| 2019/0224306 | A1 | 7/2019 | Moore et al. |

(Continued)

FOREIGN PATENT DOCUMENTS

| CA | 2905571 | 9/2014 |
| CN | 105214080 | 1/2016 |

(Continued)

OTHER PUBLICATIONS

International Search Report and Written Opinion issued for Application No. PCT/US2016/058976, dated Apr. 6, 2017, 11 pages.
International Preliminary Report on Patentability issued for Application No. PCT/US2016/058976, dated May 11, 2018.
International Search Report issued for Application No. PCT/US2014/027447 mailed on Aug. 4, 2014 (7 pages).
Extended European Search Report issued for Application No. 16860742.2, dated May 7, 2019.
Communication Pursuant to article 94(3) EPC, issued for Application No. 16860742.2, dated Jun. 3, 2022.

(Continued)

*Primary Examiner* — Shanon A. Foley
*Assistant Examiner* — Myron G Hill
(74) *Attorney, Agent, or Firm* — Meunier Carlin & Curfman LLC

(57) ABSTRACT

This disclosure relates to chimeric respiratory syncytial virus (RSV), live attenuated vaccine and immunogenic compositions, and methods of use. In certain embodiments, the chimeric respiratory syncytial virus has a mutated gene pattern encoding an RSV F protein having M at position 79, R at position 191, K at position 357, and/or Y at position 371.

16 Claims, 9 Drawing Sheets

Specification includes a Sequence Listing.

(56) References Cited

U.S. PATENT DOCUMENTS

2021/0100893 A1 4/2021 Moore et al.
2023/0293667 A1 9/2023 Pushko et al.

FOREIGN PATENT DOCUMENTS

| JP | 2012-511579 A | 5/2012 | |
|---|---|---|---|
| WO | 0189562 | 11/2001 | |
| WO | 2006042156 | 4/2006 | |
| WO | 2008121992 | 10/2008 | |
| WO | 2010053883 | 3/2010 | |
| WO | 2012158613 | 11/2012 | |
| WO | 2014124238 | 8/2014 | |
| WO | 2014152534 | 9/2014 | |
| WO | WO-2014152534 A1 * | 9/2014 | ............ A61K 39/12 |
| WO | 2014160463 | 10/2014 | |

OTHER PUBLICATIONS

Buchholz, Ursula J., et al. "Deletion of nonstructural proteins NS1 and NS2 from pneumonia virus of mice attenuates viral replication and reduces pulmonary cytokine expression and disease." Journal of virology 83.4 (2009): 1969-1980.
Burns, Cara Carthel, et al. "Modulation of poliovirus replicative fitness in HeLa cells by deoptimization of synonymous codon usage in the capsid region." Journal of virology 80.7 (2006): 3259-3272.
Clements, Mary Lou, et al. "Evaluation of bovine, cold-adapted human, and wild-type human parainfluenza type 3 viruses in adult volunteers and in chimpanzees." Journal of clinical microbiology 29.6 (1991): 1175-1182.
Coleman, J. Robert, et al. "Virus attenuation by genome-scale changes in codon pair bias." Science 320.5884 (2008): 1784-1787.
Collins, Peter L., and José A. Melero. "Progress in understanding and controlling respiratory syncytial virus: still crazy after all these years." Virus research 162.1-2 (2011): 80-99.
Collins, Peter L., et al. "Gene overlap and site-specific attenuation of transcription of the viral polymerase L gene of human respiratory syncytial virus." Proceedings of the National Academy of Sciences 84.15 (1987): 5134-5138.
Collins, Peter L., et al. "Nucleotide sequences for the gene junctions of human respiratory syncytial virus reveal distinctive features of intergenic structure and gene order." Proceedings of the National Academy of Sciences 83.13 (1986): 4594-4598.
Collins, Peter L., et al. "Production of infectious human respiratory syncytial virus from cloned cDNA confirms an essential role for the transcription elongation factor from the 5'proximal open reading frame of the M2 mRNA in gene expression and provides a capability for vaccine development." Proceedings of the National Academy of Sciences 92.25 (1995): 11563-11567.
DeWet, J. R., et al. "Subramani (1987)." Firefly luciferase gene: structure and expression in mammalian cells. Mol. Cell. Biol 7.725-737.
EMBL: U39661, Respiratory syncytial virus, complete genome. [online] Mar. 29, 1997.
European Search Report in Application No. 14770291.4 mailed on Jan. 23, 2017 (10 pages).
First Examination Report issued by the Australian Patent Office, in Application No. 2014239583, dated Jun. 18, 2019.
Examination Report No. 2 for Australian Application No. 2014239583 dated May 26, 2020.
First Examination Report issued by the Australian Patent Office, in Application No. 2020244533, dated Apr. 11, 2022.
First Office Action issued by the Japanese Patent Office, in Application No. 22016-502442, dated Jun. 5, 2018 (5 pages) English Translation.
Glenn, Gregory M., et al. "A randomized, blinded, controlled, dose-ranging study of a respiratory syncytial virus recombinant fusion (F) nanoparticle vaccine in healthy women of childbearing age." The Journal of infectious diseases 213.3 (2015): 411-422.

Hotard et al. A stabilized respiratory syncytial virus reverse genetics system amenable to recombination-mediated mutagenesis. Virology 434, 129-136 (2012).
Hotard et al. Identification of residues in the human respiratory syncytial virus fusion protein that modulate fusion activity and pathogenesis. J Virol 89, 512-522 (2015).
Hotard, Anne L., et al. "Functional analysis of the 60-nucleotide duplication in the respiratory syncytial virus Buenos Aires strain attachment glycoprotein." Journal of virology 89.16 (2015): 8258-8266.
Iyer, Vidyashankara, et al. "Impact of formulation and particle size on stability and immunogenicity of oil-in-water emulsion adjuvants." Human vaccines & immunotherapeutics 11.7 (2015): 1853-1864.
Johnson, Philip R., et al. "The G glycoprotein of human respiratory syncytial viruses of subgroups A and B: extensive sequence divergence between antigenically related proteins." Proceedings of the National Academy of Sciences 84.16 (1987): 5625-5629.
Karron, R. A., et al. "A gene deletion that up-regulates viral gene expression yields an attenuated RSV vaccine with improved antibody responses in children. Sci Transl Med 7: 312ra175." (2015).
Karron, Ruth A., et al. "Identification of a recombinant live attenuated respiratory syncytial virus vaccine candidate that is highly attenuated in infants." The Journal of infectious diseases 191.7 (2005): 1093-1104.
Kim, Hyun Wha, et al. "Respiratory syncytial virus disease in infants despite prior administration of antigenic inactivated vaccine." American journal of epidemiology 89.4 (1969): 422-434.
Kim, Hyun Wha, et al. "Safety and antigenicity of temperature sensitive (TS) mutant respiratory syncytial virus (RSV) in infants and children." Pediatrics 52.1 (1973): 56-63.
Lemon, Ken, et al. "Recombinant subgroup B human respiratory syncytial virus expressing enhanced green fluorescent protein efficiently replicates in primary human cells and is virulent in cotton rats." Journal of virology 89.5 (2015): 2849-2856.
Maniatis, Tom, Stephen Goodbourn, and Janice A. Fischer. "Regulation of inducible and tissue-specific gene expression." Science 236.4806 (1987): 1237-1245.
Meng et al. Respiratory Syncytial Virus Attachment Glycoprotein Contribution to Infection Depends on the Specific Fusion Protein. Journal of virology 90, 245-253 (2015).
Meng, Jia, et al. "Refining the balance of attenuation and immunogenicity of respiratory syncytial virus by targeted codon deoptimization of virulence genes." MBio 5.5 (2014): e01704-14.
Merzlyak, Ekaterina M., et al. "Bright monomeric red fluorescent protein with an extended fluorescence lifetime." Nature methods 4.7 (2007): 555.
Moore, Martin L., et al. "A chimeric A2 strain of respiratory syncytial virus (RSV) with the fusion protein of RSV strain line 19 exhibits enhanced viral load, mucus, and airway dysfunction." Journal of virology 83.9 (2009): 4185-4194.
Mueller, Steffen, et al. "Reduction of the rate of poliovirus protein synthesis through large-scale codon deoptimization causes attenuation of viral virulence by lowering specific infectivity." Journal of virology 80.19 (2006): 9687-9696.
Murphy, Brian R., et al. "Enhanced pulmonary histopathology is observed in cotton rats immunized with formalin-inactivated respiratory syncytial virus (RSV) or purified F glycoprotein and challenged with RSV 3-6 months after immunization." Vaccine 8.5 (1990): 497-502.
NCBI, GenBank Accession No. ACO83297.1, Apr. 20, 2009.
NCBI, GenBank Accession No. U50362.1, Jun. 30, 2004.
Needleman, Saul B., and Christian D. Wunsch. "A general method applicable to the search for similarities in the amino acid sequence of two proteins." Journal of molecular biology 48.3 (1970): 443-453.
Office Action issued by the Chinese Patent Office, in Application No. 201480025415.2, dated Jun. 27, 2019.
Pearson, William R., and David J. Lipman. "Improved tools for biological sequence comparison." Proceedings of the National Academy of Sciences 85.8 (1988): 2444-2448.

(56) References Cited

OTHER PUBLICATIONS

Quan, Fu-Shi, et al. "Viruslike particle vaccine induces protection against respiratory syncytial virus infection in mice." Journal of Infectious Diseases 204.7 (2011): 987-995.
Randhawa, J. S., et al. "Nucleotide sequences of the genes encoding the putative attachment glycoprotein (G) of mouse and tissue culture-passaged strains of pneumonia virus of mice." Virology 207.1 (1995): 240-245.
Rostad, Christina A., et al. "A recombinant respiratory syncytial virus vaccine candidate attenuated by a low-fusion F protein is immunogenic and protective against challenge in cotton rats." Journal of virology 90.16 (2016): 7508-7518.
Shcherbo, Dmitry, et al. "Far-red fluorescent tags for protein imaging in living tissues." Biochemical journal 418.3 (2009): 567-574.
Smith, Temple F., and Michael S. Waterman. "Comparison of biosequences." Advances in applied mathematics 2.4 (1981): 482-489.
Spann, Kirsten M., Kim C. Tran, and Peter L. Collins. "Effects of nonstructural proteins NS1 and NS2 of human respiratory syncytial virus on interferon regulatory factor 3, NF-κB, and proinflammatory cytokines." Journal of virology 79.9 (2005): 5353-5362.
Stobart, Christopher C., et al. "Reverse Genetics of Respiratory Syncytial Virus." Human Respiratory Syncytial Virus. Humana Press, New York, NY, 2016. 141-153.
Title: US-14-775-671-SEQ 4 Alignment versus 08-962-690-SEQ12, 17 pages, dated Sep. 28, 2017.
Voss, Stephan D., Uwe Schlokat, and Peter Gruss. "The role of enhancers in the regulation of cell-type-specific transcriptional control." Trends in Biochemical Sciences 11.7 (1986): 287-289.
Walsh, Edward E., et al. "Immunization with glycoprotein subunits of respiratory syncytial virus to protect cotton rats against viral infection." Journal of Infectious Diseases 155.6 (1987): 1198-1204.
Wright, Peter F., et al. "Administration of a highly attenuated, live respiratory syncytial virus vaccine to adults and children." Infection and Immunity 37.1 (1982): 397-400.
Wright, Peter F., et al. "Evaluation of a live, attenuated respiratory syncytial virus vaccine in infants." The Journal of pediatrics 88.6 (1976): 931-936.
English Summary of Third Office Action issued Oct. 8, 2019, for Chinese Application No. 2014800254152.
English Machine Translation of Office Action issued Dec. 3, 2019, for Japanese Application No. 2019-063498.
Search Report and Written Opinion issued Sep. 10, 2019, for Singaporean Application No. 11201803581V.
Examination Report issued in Singaporean Application No. 11201803581V dated Dec. 2, 2020.
Notice of Allowance mailed Jan. 10, 2020, in U.S. Appl. No. 16/263,915.
Notice of Allowance mailed May 28, 2020, in U.S. Appl. No. 16/263,915.
Boyapalle et al. Respiratory Syncytial Virus NS1 Protein Colocalizes with Mitochondrial Antiviral Signaling Protein MAVS following Infection, PLoS One 7(2): e29386. doi: 10.1371/journal.pone.0029386, 201.
Office Action mailed Jan. 27, 2020, for Canadian Application No. 2,906,606.
Second Written Opinion for Singaporean Application No. 11201803581V dated Jun. 15, 2020.
English summary of Decision of Rejection issued for Chinese Application No. 2014800254152, dated Jul. 13, 2020.
English translation of Notice of Reasons for Refusal for Japanese Application No. 2019-063498 dated Oct. 27, 2020.
English translation of Office Action for Japanese Application No. 2018-522569 dated Nov. 4, 2020.
English translation of Office Action for Japanese Application No. 2018-522569 dated Jun. 7, 2022.
English translation of Office Action for Japanese Application No. 2018-522569 Dec. 28, 2022.
Examination Report for Singaporean Application No. 11201803581V dated Dec. 2, 2020.
English translation of Preliminary Office Action for Brazilian Application No. BR112018008708-4 dated Jan. 19, 2021.
Office Action issued in Canadian Application No. 2,906,606 dated Feb. 1, 2021.
Extended European Search Report for Application No. 20203964 dated Feb. 23, 2021.
Dochow, Melanie, et al. "Independent structural domains in paramyxovirus polymerase protein." Journal of Biological Chemistry 287.9 (2012): 6878-6891.
Teng, N. Michael. "The non-structural proteins of RSV: targeting interferon antagonists for vaccine development." Infectious Disorders-Drug Targets (Formerly Current Drug Targets-Infectious Disorders) 12.2 (2012): 129-137.
Luongo, Cindy, et al. "Increased genetic and phenotypic stability of a promising live-attenuated respiratory syncytial virus vaccine candidate by reverse genetics." Journal of virology 86.19 (2012): 10792-10804.
English Translations of Office Action and Search report issued for Chinese Application No. 201680072681, dated Dec. 7, 2021.
English Translations of Second Office Action issued for Chinese Application No. 201680072681, dated Sep. 28, 2022.
English Summary of office action issued in Mexican application No. MX/a/2018/005462, mailed Apr. 12, 2022.
English translation of Decision of Rejection issued in Chinese Application No. 201680072681.X, mailed May 10, 2023.
English translation of Decision to Grant issued in Japanese Application No. 2018-522569, mailed Jun. 6, 2023.
English translation of Decision of Rejection issued in Chinese Application No. 202110603289.6, mailed Jun. 9, 2023.
Ternette et al., Immunogenicity and efficacy of codon optimized DNA vaccines encoding the F-protein of respiratory syncytial virus, Vaccine 25 (2007) 7271-7279.
Non Final Office Action issued in Co-pending U.S. Appl. No. 18/046,743, mailed Aug. 3, 2023.
English translation of Notice of Reasons of Refusal issued in Japanese Patent Application No. 2023-025816, mailed Nov. 19, 2024.

* cited by examiner

```
Query    1    MELPILKANAITTILAAVTFCFASSQNITEEFYQSTCSAVSKGYLSALRTGWYTSVITIE    60
              MELPILKANAITTILAAVTFCFASSQNITEEFYQSTCSAVSKGYLSALRTGWYTSVITIE
Sbjct    1    MELPILKANAITTILAAVTFCFASSQNITEEFYQSTCSAVSKGYLSALRTGWYTSVITIE    60

Query   61    LSNIKKNKCNGTDAKVKLMKQELDKYKNAVTELQLLMQSTPAANNRARRELPRFMNYTLN   120
              LSNIKKNKCNGTDAKVKLMKQELDKYKNAVTELQLLMQSTPAANNRARRELPRFMNYTLN
Sbjct   61    LSNIKKNKCNGTDAKVKLMKQELDKYKNAVTELQLLMQSTPAANNRARRELPRFMNYTLN   120

Query  121    NTKKTNVTLSKKRKRRFLGFLLGVGSAIASGIAVSKVLHLEGEVNKIKSALLSTNKAVVS   180
              NTKKTNVTLSKKRKRRFLGFLLGVGSAIASGIAVSKVLHLEGEVNKIKSALLSTNKAVVS
Sbjct  121    NTKKTNVTLSKKRKRRFLGFLLGVGSAIASGIAVSKVLHLEGEVNKIKSALLSTNKAVVS   180

Query  181    LSNGVSVLTSRVLDLKNYIDKQLLPIVNKQSCRISNIETVIEFQQKNNRLLEITREFSVN   240
              LSNGVSVLTSRVLDLKNYIDKQLLPIVNKQSCRISNIETVIEFQQKNNRLLEITREFSVN
Sbjct  181    LSNGVSVLTSRVLDLKNYIDKQLLPIVNKQSCRISNIETVIEFQQKNNRLLEITREFSVN   240

Query  241    AGVTTPVSTYMLTNSELLSLINDMPITNDQKKLMSNNVQIVRQQSYSIMSIIKEEVLAYV   300
              AGVTTPVSTYMLTNSELLSLINDMPITNDQKKLMSNNVQIVRQQSYSIMSIIKEEVLAYV
Sbjct  241    AGVTTPVSTYMLTNSELLSLINDMPITNDQKKLMSNNVQIVRQQSYSIMSIIKEEVLAYV   300

Query  301    VQLPLYGVIDTPCWKLHTSPLCTTNTKEGSNICLTRTDRGWYCDNAGSVSFFPQAEKCKV   360
              VQLPLYGVIDTPCWKLHTSPLCTTNTKEGSNICLTRTDRGWYCDNAGSVSFFPQAEKCKV
Sbjct  301    VQLPLYGVIDTPCWKLHTSPLCTTNTKEGSNICLTRTDRGWYCDNAGSVSFFPQAEKCKV   360

Query  361    QSNRVFCDTMYSLTLPSEVNLCNVDIFNPKYDCKIMTSKTDVSSSVITSLGAIVSCYGKT   420
              QSNRVFCDTMYSLTLPSEVNLCNVDIFNPKYDCKIMTSKTDVSSSVITSLGAIVSCYGKT
Sbjct  361    QSNRVFCDTMYSLTLPSEVNLCNVDIFNPKYDCKIMTSKTDVSSSVITSLGAIVSCYGKT   420

Query  421    KCTASNKNRGIIKTFSNGCDYVSNKGVDTVSVGNTLYYVNKQEGKSLYVKGEPIINFYDP   480
              KCTASNKNRGIIKTFSNGCDYVSNKGVDTVSVGNTLYYVNKQEGKSLYVKGEPIINFYDP
Sbjct  421    KCTASNKNRGIIKTFSNGCDYVSNKGVDTVSVGNTLYYVNKQEGKSLYVKGEPIINFYDP   480

Query  481    LVFPSDEFDASISQVNEKINQSLAFIRKSDELLHNVNAGKSTTNIMITTIIVIIVILLS   540
              LVFPSDEFDASISQVNEKINQSLAFIRKSDELLHNVNAGKSTTNIMITTIIVIIVILLS
Sbjct  481    LVFPSDEFDASISQVNEKINQSLAFIRKSDELLHNVNAGKSTTNIMITTIIVIIVILLS   540

Query  541    LIAVGLLLYCKARSTPVTLSKDQLSGINNIAFSN        (SEQ ID NO: 3)
              LIAVGLLLYCKARSTP+TLSKDQLSGINNIAFSN
Sbjct  541    LIAVGLLLYCKARSTPITLSKDQLSGINNIAFSN            (SEQ ID NO: 4)
```

FIG. 1

```
Query    1    MELLIHRSSAIFLTLAINALYLTSSQNITEEFYQSTCSAVSRGYLSALRTGWYTSVITIE    60
              MELLIHRSSAIFLTLAINALYLTSSQNITEEFYQSTCSAVSRGYLSALRTGWYTSVITIE
Sbjct    1    MELLIHRSSAIFLTLAINALYLTSSQNITEEFYQSTCSAVSRGYLSALRTGWYTSVITIE    60

Query    61   LSNIKETKCNGTDTKVKLMKQELDKYKNAVTELQLLMQNTPAANNRARREAPQYMNYTIN   120
              LSNIKETKCNGTDTKVKL+KQELDKYKNAVTELQLLMQNTPAANNRARREAPQYMNYTIN
Sbjct    61   LSNIKETKCNGTDTKVKLIKQELDKYKNAVTELQLLMQNTPAANNRARREAPQYMNYTIN   120

Query    121  TTKNLNVSISKKRKRRFLGFLLGVGSAIASGIAVSKVLHLEGEVNKIKNALLSTNKAVVS   180
              TTKNLNVSISKKRKRRFLGFLLGVGSAIASGIAVSKVLHLEGEVNKIKNALLSTNKAVVS
Sbjct    121  TTKNLNVSISKKRKRRFLGFLLGVGSAIASGIAVSKVLHLEGEVNKIKNALLSTNKAVVS   180

Query    181  LSNGVSVLTSRVLDLKNYINNQLLPIVNQQSCRISNIETVIEFQQKNSRLLEITREFSVN   240
              LSNGVSVLTS+VLDLKNYINNQLLPIVNQQSCRISNIETVIEFQQKNSRLLEITREFSVN
Sbjct    181  LSNGVSVLTSKVLDLKNYINNQLLPIVNQQSCRISNIETVIEFQQKNSRLLEITREFSVN   240

Query    241  AGVTTPLSTYMLTNSELLSLINDMPITNDQKKLMSSNVQIVRQQSYSIMSIIKEEVLAYV   300
              AGVTTPLSTYMLTNSELLSLINDMPITNDQKKLMSSNVQIVRQQSYSIMSIIKEEVLAYV
Sbjct    241  AGVTTPLSTYMLTNSELLSLINDMPITNDQKKLMSSNVQIVRQQSYSIMSIIKEEVLAYV   300

Query    301  VQLPIYGVIDTPCWKLHTSPLCTTNIKEGSNICLTRTDRGWYCDNAGSVSFFPQADKCKV   360
              VQLPIYGVIDTPCWKLHTSPLCTTNIKEGSNICLTRTDRGWYCDNAGSVSFFPQAD CKV
Sbjct    301  VQLPIYGVIDTPCWKLHTSPLCTTNIKEGSNICLTRTDRGWYCDNAGSVSFFPQADTCKV   360

Query    361  QSNRVFCDTMYSLTLPSEVSLCNTDIFNSKYDCKIMTSKTDISSSVITSLGAIVSCYGKT   420
              QSNRVFCDTM SLTLPSEVSLCNTDIFNSKYDCKIMTSKTDISSSVITSLGAIVSCYGKT
Sbjct    361  QSNRVFCDTMNSLTLPSEVSLCNTDIFNSKYDCKIMTSKTDISSSVITSLGAIVSCYGKT   420

Query    421  KCTASNKNRGIIKTFSNGCDYVSNKGVDTVSVGNTLYYVNKLEGKNLYVKGEPIINYYDP   480
              KCTASNKNRGIIKTFSNGCDYVSNKGVDTVSVGNTLYYVNKLEGKNLYVKGEPIINYYDP
Sbjct    421  KCTASNKNRGIIKTFSNGCDYVSNKGVDTVSVGNTLYYVNKLEGKNLYVKGEPIINYYDP   480

Query    481  LVFPSDEFDASISQVNEKINQSLAFIRRSDELLHNVNTGKSTTNIMITAIIIVIIVVLLS   540
              LVFPSDEFDASISQVNEKINQSLAFIRRSDELLHNVNTGKSTTNIMITAIIIVIIVVLLS
Sbjct    481  LVFPSDEFDASISQVNEKINQSLAFIRRSDELLHNVNTGKSTTNIMITAIIIVIIVVLLS   540

Query    541  LIAIGLLLYCKAKNTPVTLSKDQLSGINNIAFS      (SEQ ID NO:1)
              LIAIGLLLYCKAKNTPVTLSKDQLSGINNIAFS
Sbjct    541  LIAIGLLLYCKAKNTPVTLSKDQLSGINNIAFS        (SEQ ID NO: 2)
```

FIG. 5A

```
Query    1    MELLIHRSSAIFLTLAINALYLTSSQNITEEFYQSTCSAVSRGYLSALRTGWYTSVITIE    60
              MEL I +++AI    LA       SSQNITEEFYQSTCSAVS+GYLSALRTGWYTSVITIE
Sbjct    1    MELPILKANAITTILAAVTFCFASSQNITEEFYQSTCSAVSKGYLSALRTGWYTSVITIE    60

Query    61   LSNIKETKCNGTDTKVKLMKQELDKYKNAVTELQLLMQNTPAANNRARREAPQYMNYTIN    120
              LSNIK+ KCNGTD KVKLMKQELDKYKNAVTELQLLMQ+TPAANNRARRE P++MNYT+N
Sbjct    61   LSNIKKNKCNGTDAKVKLMKQELDKYKNAVTELQLLMQSTPAANNRARRELPRFMNYTLN    120

Query    121  TTKNLNVSISKKRKRRFLGFLLGVGSAIASGIAVSKVLHLEGEVNKIKNALLSTNKAVVS    180
              TK  NV++SKKRKRRFLGFLLGVGSAIASGIAVSKVLHLEGEVNKIK+ALLSTNKAVVS
Sbjct    121  NTKKTNVTLSKKRKRRFLGFLLGVGSAIASGIAVSKVLHLEGEVNKIKSALLSTNKAVVS    180

Query    181  LSNGVSVLTSRVLDLKNYINNQLLPIVNQQSCRISNIETVIEFQQKNSRLLEITREFSVN    240
              LSNGVSVLTSRVLDLKNYI+ QLLPIVN+QSCRISNIETVIEFQQKN+RLLEITREFSVN
Sbjct    181  LSNGVSVLTSRVLDLKNYIDKQLLPIVNKQSCRISNIETVIEFQQKNNRLLEITREFSVN    240

Query    241  AGVTTPLSTYMLTNSELLSLINDMPITNDQKKLMSSNVQIVRQQSYSIMSIIKEEVLAYV    300
              AGVTTP+STYMLTNSELLSLINDMPITNDQKKLMS+NVQIVRQQSYSIMSIIKEEVLAYV
Sbjct    241  AGVTTPVSTYMLTNSELLSLINDMPITNDQKKLMSNNVQIVRQQSYSIMSIIKEEVLAYV    300

Query    301  VQLPIYGVIDTPCWKLHTSPLCTTNIKEGSNICLTRTDRGWYCDNAGSVSFFPQADKCKV    360
              VQLP+YGVIDTPCWKLHTSPLCTTN KEGSNICLTRTDRGWYCDNAGSVSFFPQA+KCKV
Sbjct    301  VQLPLYGVIDTPCWKLHTSPLCTTNTKEGSNICLTRTDRGWYCDNAGSVSFFPQAEKCKV    360

Query    361  QSNRVFCDTMYSLTLPSEVSLCNTDIFNSKYDCKIMTSKTDISSSVITSLGAIVSCYGKT    420
              QSNRVFCDTMYSLTLPSEV+LCN DIFN KYDCKIMTSKTD+SSSVITSLGAIVSCYGKT
Sbjct    361  QSNRVFCDTMYSLTLPSEVNLCNVDIFNPKYDCKIMTSKTDVSSSVITSLGAIVSCYGKT    420

Query    421  KCTASNKNRGIIKTFSNGCDYVSNKGVDTVSVGNTLYYVNKLEGKNLYVKGEPIINYYDP    480
              KCTASNKNRGIIKTFSNGCDYVSNKGVDTVSVGNTLYYVNK EGK+LYVKGEPIIN+YDP
Sbjct    421  KCTASNKNRGIIKTFSNGCDYVSNKGVDTVSVGNTLYYVNKQEGKSLYVKGEPIINFYDP    480

Query    481  LVFPSDEFDASISQVNEKINQSLAFIRRSDELLHNVNTGKSTTNIMITAIIIVIIVVLLS    540
              LVFPSDEFDASISQVNEKINQSLAFIR+SDELLHNVN GKSTTNIMIT IIIVIIV+LLS
Sbjct    481  LVFPSDEFDASISQVNEKINQSLAFIRKSDELLHNVNAGKSTTNIMITTIIIVIIVILLS    540

Query    541  LIAIGLLLYCKAKNTPVTLSKDQLSGINNIAFS    (SEQ ID NO:1)

LIA+GLLLYCKA++TP+TLSKDQLSGINNIAFS
Sbjct    541  LIAVGLLLYCKARSTPITLSKDQLSGINNIAFS    (SEQ ID NO:4)
```

FIG. 5B

SEQUENCE LISTING

<160> NUMBER OF SEQ ID NOS: 15

<210> SEQ ID NO 1
<211> LENGTH: 573
<212> TYPE: PRT
<213> ORGANISM: Artificial
<220> FEATURE:
<223> OTHER INFORMATION: Synthetic

<400> SEQUENCE: 1

```
Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
```

```
            130                 135                 140
Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Arg Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Lys Cys Lys Val Gln Ser Asn Arg Val Phe Cys Asp
        355                 360                 365

Thr Met Tyr Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Ala Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560
```

```
Lys Asp Gln Leu Ser Gly Ile Asn Asn Ile Ala Phe Ser
            565                 570
```

<210> SEQ ID NO 2
<211> LENGTH: 573
<212> TYPE: PRT
<213> ORGANISM: Artificial
<220> FEATURE:
<223> OTHER INFORMATION: Synthetic

<400> SEQUENCE: 2

```
Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

-continued

```
Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
    515                 520                 525

Ala Ile Ile Ile Val Ile Ile Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser
            565                 570
```

<210> SEQ ID NO 3
<211> LENGTH: 574
<212> TYPE: PRT
<213> ORGANISM: Artificial
<220> FEATURE:
<223> OTHER INFORMATION: Synthetic

<400> SEQUENCE: 3

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Met Lys
65              70                  75                  80

Gln Glu Leu Asp Lys Tyr Lys Asn Ala Val Thr Glu Leu Gln Leu Leu
            85                  90                  95

Met Gln Ser Thr Pro Ala Ala Asn Asn Arg Ala Arg Arg Glu Leu Pro
        100                 105                 110

Arg Phe Met Asn Tyr Thr Leu Asn Asn Thr Lys Lys Thr Asn Val Thr
    115                 120                 125

Leu Ser Lys Lys Arg Lys Arg Arg Phe Leu Gly Phe Leu Leu Gly Val
130                 135                 140
```

-continued

```
Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Arg Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Lys Cys Lys Val Gln Ser Asn Arg Val Phe Cys Asp
            355                 360                 365

Thr Met Tyr Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560
```

Lys Asp Gln Leu Ser Gly Ile Asn Asn Ile Ala Phe Ser Asn
            565                 570

<210> SEQ ID NO 4
<211> LENGTH: 574
<212> TYPE: PRT
<213> ORGANISM: Artificial
<220> FEATURE:
<223> OTHER INFORMATION: Synthetic

<400> SEQUENCE: 4

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Arg Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

```
Pro Gln Ala Glu Lys Cys Lys Val Gln Ser Asn Arg Val Phe Cys Asp
            355                 360                 365
Thr Met Tyr Ser Leu Thr Leu Pro Ser Glu Val Asn Leu Cys Asn Val
    370                 375                 380
Asp Ile Phe Asn Pro Lys Tyr Asp Cys Lys Ile Met Thr Ser Lys Thr
385                 390                 395                 400
Asp Val Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Val Asn Lys Gln Glu Gly
    450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
                500                 505                 510
Leu His Asn Val Asn Ala Gly Lys Ser Thr Thr Asn Ile Met Ile Thr
            515                 520                 525
Thr Ile Ile Ile Val Ile Ile Val Ile Leu Leu Ser Leu Ile Ala Val
            530                 535                 540
Gly Leu Leu Leu Tyr Cys Lys Ala Arg Ser Thr Pro Ile Thr Leu Ser
545                 550                 555                 560
Lys Asp Gln Leu Ser Gly Ile Asn Asn Ile Ala Phe Ser Asn
                565                 570

<210> SEQ ID NO 5
<211> LENGTH: 74
<212> TYPE: DNA
<213> ORGANISM: Artificial
<220> FEATURE:
<223> OTHER INFORMATION: Synthetic

<400> SEQUENCE: 5
agatctagta ctcaaataag ttaataaaaa atatacacat ggacgtccat cctgttgaca    60
attaatcatc ggca                                                     74

<210> SEQ ID NO 6
<211> LENGTH: 70
<212> TYPE: DNA
<213> ORGANISM: Artificial
<220> FEATURE:
<223> OTHER INFORMATION: Synthetic

<400> SEQUENCE: 6
gtcttagcgg tgcgttggtc cttgttttg gacatgtttg catttgcccc tcagcactgt    60
cctgctcctt                                                          70

<210> SEQ ID NO 7
<211> LENGTH: 100
<212> TYPE: DNA
<213> ORGANISM: Artificial
<220> FEATURE:
<223> OTHER INFORMATION: Synthetic

<400> SEQUENCE: 7
```
agatctagta ctcaaataag ttaataaaaa atatacacat ggacgtccat ggggcaaatg    60
caaacatgtc caaaaacaag gaccaacgca ccgctaagac                          100

<210> SEQ ID NO 8
<211> LENGTH: 100
<212> TYPE: DNA
<213> ORGANISM: Artificial
<220> FEATURE:
<223> OTHER INFORMATION: Synthetic

<400> SEQUENCE: 8
gtcttagcgg tgcgttggtc cttgtttttg gacatgtttg catttgcccc atggacgtcc    60
atgtgtatat tttttattaa cttatttgag tactagatct                          100

<210> SEQ ID NO 9
<211> LENGTH: 74
<212> TYPE: DNA
<213> ORGANISM: Artificial
<220> FEATURE:
<223> OTHER INFORMATION: Synthetic

<400> SEQUENCE: 9
ttagtgatac aaatgaccat gccaaaaata atgatactac ctgacaaata cctgttgaca    60
attaatcatc ggca                                                      74

<210> SEQ ID NO 10
<211> LENGTH: 70
<212> TYPE: DNA
<213> ORGANISM: Artificial
<220> FEATURE:
<223> OTHER INFORMATION: Synthetic

<400> SEQUENCE: 10
attgtttgaa ttaataatgt aacgatgtgg tgagtgttag aattgagtgt tcagcactgt    60
cctgctcctt                                                           70

<210> SEQ ID NO 11
<211> LENGTH: 100
<212> TYPE: DNA
<213> ORGANISM: Artificial
<220> FEATURE:
<223> OTHER INFORMATION: Synthetic

<400> SEQUENCE: 11
ttagtgatac aaatgaccat gccaaaaata atgatactac ctgacaaata acactcaatt    60
ctaacactca ccacatcgtt acattattaa ttcaaacaat                          100

<210> SEQ ID NO 12
<211> LENGTH: 100
<212> TYPE: DNA
<213> ORGANISM: Artificial
<220> FEATURE:
<223> OTHER INFORMATION: Synthetic

<400> SEQUENCE: 12
attgtttgaa ttaataatgt aacgatgtgg tgagtgttag aattgagtgt tatttgtcag    60
gtagtatcat tattttggc atggtcattt gtatcactaa                           100

<210> SEQ ID NO 13
<211> LENGTH: 524
<212> TYPE: PRT

<213> ORGANISM: Artificial
<220> FEATURE:
<223> OTHER INFORMATION: Synthetic

<400> SEQUENCE: 13

```
Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Arg Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Lys Cys Lys Val Gln Ser Asn Arg Val Phe Cys Asp
        355                 360                 365

Thr Met Tyr Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
```

```
                385                 390                 395                 400
Asp Ile Ser Ser Ser Val Ile Thr Ser Leu Gly Ala Ile Val Ser Cys
                    405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn
        515                 520

<210> SEQ ID NO 14
<211> LENGTH: 1725
<212> TYPE: DNA
<213> ORGANISM: Artificial
<220> FEATURE:
<223> OTHER INFORMATION: Synthetic

<400> SEQUENCE: 14
atggagttgc tgatccatag atcaagtgca atcttcctaa ctcttgctat taatgcattg      60
tacctcacct caagtcagaa cataactgag gagttttacc aatcgacatg tagtgcagtt     120
agcagaggtt acttgagtgc tttaagaaca ggttggtata ccagtgtcat aacaatagaa     180
ttaagtaata taaagaaaac caaatgcaat ggaactgaca ctaaagtaaa acttataaaa     240
caagaattag ataagtataa gaatgcagta acagaattac agttacttat gcaaacacac     300
ccagctgcca caaccgggc cagaagagaa gcaccacagt atatgaacta cacaatcaat     360
accactaaaa acctaaatgt atcaataagc aagaagagga aacgaagatt tctgggcttc     420
ttgttaggtg taggatctgc aatagcaagt ggtatagctg tatccaaagt tctacacctt     480
gaaggagaag tgaacaagat caaaaatgct ttgctgtcta caaacaaagc tgtagtcagt     540
ctatcaaatg gggtcagtgt tttaaccagc aaagtgttag atctcaagaa ttatataaac     600
aaccaattat acctatagt aaatcaacag agttgtcgca tttccaacat gaaacagtt     660 atagaattcc agcagaagaa cagcagattg ttggaaatca ccagagaatt tagtgtcaat     720
gcaggtgtaa cgacaccttt aagcacttac atgttaacaa cagtgagtt actatcatta     780 atcaatgata tgcctataac aaatgatcag aaaaaattaa tgtcaagcaa tgttcagata     840
gtaaggcaac aaagttattc tatcatgtct ataataaagg aagaagtcct tgcatatgtt     900
gtacagctac ctatctatgg tgtaattgat acaccttgct ggaaattaca cacatcacct     960
ctgtgcacca ccaacatcaa agaaggatca atatttgtt taacaaggac tgatagagga    1020
tggtactgtg ataatgcagg atcagtatcc ttctttccac aggctgacac ttgtaaagta    1080
cagtccaatc gagtattttg tgacactatg aacagtttga cattaccaag tgaagtcagc    1140
ctttgtaaca ctgacatatt caattccaag tatgactgca aaattatgac atcaaaaaca    1200
gacataagca gctcagtaat tacttctcta ggagctatag tgtcatgcta tggtaaaact    1260
aaatgcactg catccaacaa aaatcgtgga attataaaga cattttctaa tggttgtgat    1320
```

| | | | |
|---|---|---|---|
| tatgtgtcaa | acaaaggagt | agatactgta tcagtgggca acactttata ctatgtcaac | 1380 |
| aagctggaag | gcaaaaacct | ttatgtaaaa ggggaaccta taataaatta ctatgaccct | 1440 |
| ctagtgtttc | cttctgatga | gtttgatgca tcaatatctc aagtcaatga aaaaattaat | 1500 |
| caaagtttag | cttttattcg | tagatccgat gaattattac ataatgtaaa tactggaaaa | 1560 |
| tctactacaa | atattatgat | aactgcaatt attatagtaa tcattgtagt attgttatca | 1620 |
| ttaatagcta | ttggtttact | gttgtattgc aaagccaaaa acacaccagt tacactaagc | 1680 |
| aaagaccaac | taagtggaat | caataatatt gcattcagca aatag | 1725 |

<210> SEQ ID NO 15
<211> LENGTH: 15573
<212> TYPE: DNA
<213> ORGANISM: Artificial
<220> FEATURE:
<223> OTHER INFORMATION: Synthetic

<400> SEQUENCE: 15

| | | | |
|---|---|---|---|
| acgcgaaaaa | atgcgtacaa | caaacttgca taaaccaaaa aaatgggca aataagaatt | 60 |
| tgataagtac | cacttaaatt | taactcccctt gcttagcgat ggtgagcgag ctgattaagg | 120 |
| agaacatgca | catgaagctg | tacatggagg gcaccgtgaa caaccaccac ttcaagtgca | 180 |
| catccgaggg | cgaaggcaag | ccctacgagg gcacccagac catgagaatc aaggcggtcg | 240 |
| agggcggccc | tctccccttc | gccttcgaca tcctggctac cagcttcatg tacggcagca | 300 |
| aaaccttcat | caaccacacc | cagggcatcc ccgacttctt taagcagtcc ttccccgagg | 360 |
| gcttcacatg | ggagagagtc | accacatacg aagacggggg cgtgctgacc gctacccagg | 420 |
| acaccagcct | ccaggacggc | tgcctcatct acaacgtcaa gatcagaggg gtgaacttcc | 480 |
| catccaacgg | ccctgtgatg | cagaagaaaa cactcggctg ggaggcctcc accgagaccc | 540 |
| tgtaccccgc | tgacggcggc | ctggaaggca gagccgacat ggcccctgaag ctcgtgggcg | 600 |
| ggggccacct | gatctgcaac | ttgaagacca catacagatc caagaaaccc gctaagaacc | 660 |
| tcaagatgcc | cggcgtctac | tatgtggaca agactggaa agaatcaag gaggccgaca | 720 |
| aagagaccta | cgtcgagcag | cacgaggtgg ctgtggccag atactgcgac ctccctagca | 780 |
| aactggggca | cagatgagta | ttcaattata gttattaaaa acttaacaga agacaaaaat | 840 |
| ggggcaaata | agaatttgat | aagtaccact taaatttaac tccccttgctt agcgatgggt | 900 |
| tcgaattcgc | tatcgatgat | aaaagtacgt ctacaaaatc tatttgataa tgatgaagta | 960 |
| gcgctactaa | aaataacgtg | ttatacggat aaactaatac atctaacgaa tgcgctagcg | 1020 |
| aaagcggtaa | tacatacgat | aaaactaaat ggtatagtat ttgtacatgt aataacgtcg | 1080 |
| tcggatatat | gtccgaataa | taatatagta gtaaaatcga attttacgac gatgccggta | 1140 |
| ctacaaaatg | gtggttatat | atgggaaatg atggaactaa cgcattgttc gcaaccgaat | 1200 |
| ggtctactag | atgataattg | tgaaataaaa ttttcgaaaa aactatcgga ttcgacgatg | 1260 |
| acgaattata | tgaatcaact | atcggaacta ctaggttttg atctaaatcc gtaaattata | 1320 |
| attaatatca | actagcaaat | caatgtcact aacaccatta gttaatataa aacttaacag | 1380 |
| aagacaaaaa | tggggcaaat | aaatcaattc agccaaccca accatggata cgacgcataa | 1440 |
| tgataatacg | ccgcaacgtc | taatgataac ggatatgcgt ccgctatcgc tagaaacgat | 1500 |
| aataacgtcg | ctaacgcgtg | atataataac gcataaattt atatatctaa taatcatga | 1560 |
| atgtatagta | cgtaaactag | atgaacgtca agcgacgttt acgtttctag taaattatga | 1620 |

```
aatgaaacta ctacataaag taggttcgac gaaatataaa aaatatacgg aatataatac    1680
gaaatatggt acgtttccga tgccgatatt tataaatcat gatggttttc tagaatgtat    1740
aggtataaaa ccgacgaaac atacgccgat aatatataaa tatgatctaa atccgtaaat    1800
ttcaacacaa tattcacaca atctaaaaca acaactctat gcataactat actccatagt    1860
ccagatggag cctgaaaatt atagtaattt aaaattaagg agagatataa gatagaagat    1920
ggggcaaata caaagatggc tcttagcaaa gtcaagttga atgatacact caacaaagat    1980
caacttctgt catccagcaa atacaccatc aacggagca caggagatag tattgatact    2040
cctaattatg atgtgcagaa acacatcaat aagttatgtg gcatgttatt aatcacagaa    2100
gatgctaatc ataaattcac tgggttaata ggtatgttat atgcgatgtc taggttagga    2160
agagaagaca cctataaaat actcagagat gcgggatatc atgtaaaagc aaatggagta    2220
gatgtaacaa cacatcgtca agacattaat ggaaaagaaa tgaaatttga agtgttaaca    2280
ttggcaagct taacaactga aattcaaatc aacattgaga tagaatctag aaaatcctac    2340
aaaaaaatgc taaagaaat gggagaggta gctccagaat acaggcatga ctctcctgat    2400
tgtgggatga taatattatg tatagcagca ttagtaataa ctaaattagc agcagggac    2460
agatctggtc ttacagccgt gattaggaga gctaataatg tcctaaaaaa tgaaatgaaa    2520
cgttacaaag gcttactacc caaggacata gccaacagct tctatgaagt gtttgaaaaa    2580
catccccact ttatgatgt ttttgttcat tttggtatag cacaatcttc taccagaggt    2640
ggcagtagag ttgaagggat ttttgcagga ttgtttatga atgcctatgg tgcagggcaa    2700
gtgatgttac ggtggggagt cttagcaaaa tcagttaaaa atattatgtt aggacatgct    2760
agtgtgcaag cagaaatgga acaagttgtt gaggtttatg aatatgccca aaaattgggt    2820
ggtgaagcag gattctacca tatattgaac aacccaaaag catcattatt atctttgact    2880
caatttcctc acttctccag tgtagtatta ggcaatgctg ctggcctagg cataatggga    2940
gagtacagag gtacaccgag gaatcaagat ctatatgatg cagcaaaggc atatgctgaa    3000
caactcaaag aaaatggtgt gattaactac agtgtactag acttgacagc agaagaacta    3060
gaggctatca acatcagct taatccaaaa gataatgatg tagagctttg agttaataaa    3120
aaatggggca aataaatcat catggaaaag tttgctcctg aattccatgg agaagatgca    3180
aacaacaggg ctactaaatt cctagaatca ataaagggca aattcacatc acccaaagat    3240
cccaagaaaa aagatagtat catatctgtc aactcaatag atatagaagt aaccaaagaa    3300
agccctataa catcaaattc aactattatc aacccaacaa atgagacaga tgatactgca    3360
gggaacaagc ccaattatca agaaaaacct ctagtaagtt tcaaagaaga ccctacacca    3420
agtgataatc ccttttctaa actatacaaa gaaaccatag aaacatttga taacaatgaa    3480
gaagaatcca gctattcata cgaagaaata aatgatcaga caaacgataa tataacagca    3540
agattagata ggattgatga aaaattaagt gaaatactag gaatgcttca cacattagta    3600
gtggcaagtg caggacctac atctgctcgg gatggtataa gagatgccat gattggttta    3660
agagaagaaa tgatagaaaa aatcagaact gaagcattaa tgaccaatga cagattagaa    3720
gctatggcaa gactcaggaa tgaggaaagt gaaaagatgg caaagacac atcagatgaa    3780
gtgtctctca atccaacatc agagaaattg aacaacctat tggaagggaa tgatagtgac    3840
aatgatctat cacttgaaga tttctgatta gttaccactc ttcacatcaa cacacaatac    3900
caacagaaga ccaacaaact aaccaaccca atcatccaac caaacatcca tccgccaatc    3960
agccaaacag ccaacaaaac aaccagccaa tccaaaacta accacccgga aaaaatctat    4020
```

```
aatatagtta caaaaaaagg aaagggtggg gcaaatatgg aaacatacgt gaacaagctt    4080
cacgaaggct ccacatacac agctgctgtt caatacaatg tcttagaaaa agacgatgac    4140
cctgcatcac ttacaatatg ggtgcccatg ttccaatcat ctatgccagc agatttactt    4200
ataaaagaac tagctaatgt caacatacta gtgaaacaaa tatccacacc caagggacct    4260
tcactaagag tcatgataaa ctcaagaagt gcagtgctag cacaaatgcc cagcaaattt    4320
accatatgcg ctaatgtgtc cttggatgaa agaagcaaac tagcatatga tgtaaccaca    4380
ccctgtgaaa tcaaggcatg tagtctaaca tgcctaaaat caaaaaatat gttgactaca    4440
gttaaagatc tcactatgaa gacactcaac cctacacatg atattattgc tttatgtgaa    4500
tttgaaaaca tagtaacatc aaaaaaagtc ataataccaa catacctaag atccatcagt    4560
gtcagaaata aagatctgaa cacacttgaa aatataacaa ccactgaatt caaaaatgct    4620
atcacaaatg caaaaatcat cccttactca ggattactat tagtcatcac agtgactgac    4680
aacaaaggag cattcaaata cataaagcca caaagtcaat tcatagtaga tcttggagct    4740
tacctagaaa aagaaagtat atattatgtt accacaaatt ggaagcacac agctacacga    4800
tttgcaatca aacccatgga agattaacct ttttcctcta catcagtgtg ttaattcata    4860
caaactttct acctacattc ttcacttcac catcacaatc acaaacactc tgtggttcaa    4920
ccaatcaaac aaaacttatc tgaagtccca gatcatccca agtcattgtt tatcagatct    4980
agtactcaaa taagttaata aaaatatac acatggacgt ccatggggca aatgcaaaca    5040
tgtccaaaaa caaggaccaa cgcaccgcta agacattaga aaggacctgg gacactctca    5100
atcatttatt attcatatca tcgtgcttat ataagttaaa tcttaaatct gtagcacaaa    5160
tcacattatc cattctggca atgataatct caacttcact tataattgca gccatcatat    5220
tcatagcctc ggcaaaccac aaagtcacac caacaactgc aatcatacaa gatgcaacaa    5280
gccagatcaa gaacacaacc ccaacatacc tcacccagaa tcctcagctt ggaatcagtc    5340
cctctaatcc gtctgaaatt acatcacaaa tcaccaccat actagcttca acaacaccag    5400
gagtcaagtc aaccctgcaa tccacaacag tcaagaccaa aaacacaaca caactcaaa     5460 cacaacccag caagcccacc acaaaacaac gccaaaacaa accaccaagc aaacccaata    5520
atgattttca ctttgaagtg ttcaactttg taccctgcag catatgcagc aacaatccaa    5580
cctgctgggc tatctgcaaa agaataccaa acaaaaaacc aggaaagaaa accactacca    5640
agcccacaaa aaaaccaacc ctcaagacaa ccaaaaaaga tcccaaacct caaaccacta    5700
aatcaaagga agtaccccacc accaagccca cagaagagcc aaccatcaac accaccaaaa    5760
caaacatcat aactacacta ctcacctcca acaccacagg aaatccagaa ctcacaagtc    5820
aaatggaaac cttccactca acttcctccg aaggcaatcc aagcccttct caagtctcta    5880
caacatccga gtacccatca caaccttcat ctccacccaa cacaccacgc cagtagttac    5940
ttaaaaacat attatcacaa aaggccttga ccaaccgcgg agaatcaaaa taaactctgg    6000
ggcaaataac aatggagttg ctgatccata gatcaagtgc aatcttccta actcttgcta    6060
ttaatgcatt gtacctcacc tcaagtcaga acataactga ggagttttac caatcgacat    6120
gtagtgcagt tagcagaggt tacttgagtg ctttaagaac aggttggtat accagtgtca    6180
taacaataga attaagtaat ataaagaaa ccaaatgcaa tggaactgac actaaagtaa    6240
aacttataaa acaagaatta gataagtata agaatgcagt aacagaatta cagttactta    6300
tgcaaaacac accagctgcc aacaaccggg ccagaagaga agcaccacag tatatgaact    6360
```

```
acacaatcaa taccactaaa aacctaaatg tatcaataag caagaagagg aaacgaagat   6420
ttctgggctt cttgttaggt gtaggatctg caatagcaag tggtatagct gtatccaaag   6480
ttctacacct tgaaggagaa gtgaacaaga tcaaaaatgc tttgctgtct acaaacaaag   6540
ctgtagtcag tctatcaaat ggggtcagtg ttttaaccag caaagtgtta gatctcaaga   6600
attatataaa caaccaatta ttacctatag taaatcaaca gagttgtcgc atttccaaca   6660
ttgaaacagt tatagaattc cagcagaaga acagcagatt gttggaaatc accagagaat   6720
ttagtgtcaa tgcaggtgta acgacacctt taagcactta catgttaaca aacagtgagt   6780
tactatcatt aatcaatgat atgcctataa caaatgatca gaaaaaatta atgtcaagca   6840
atgttcagat agtaaggcaa caaagttatt ctatcatgtc tataataaag gaagaagtcc   6900
ttgcatatgt tgtacagcta cctatctatg gtgtaattga tacaccttgc tggaaattac   6960
acacatcacc tctgtgcacc accaacatca agaaggatc aaatatttgt ttaacaagga   7020
ctgatagagg atggtactgt gataatgcag gatcagtatc cttctttcca caggctgaca   7080
cttgtaaagt acagtccaat cgagtatttt gtgacactat gaacagtttg acattaccaa   7140
gtgaagtcag cctttgtaac actgacatat tcaattccaa gtatgactgc aaaattatga   7200
catcaaaaac agacataagc agctcagtaa ttacttctct aggagctata gtgtcatgct   7260
atggtaaaac taaatgcact gcatccaaca aaaatcgtgg aattataaag acattttcta   7320
atggttgtga ttatgtgtca aacaaaggag tagatactgt atcagtgggc aacactttat   7380
actatgtcaa caagctggaa ggcaaaaacc tttatgtaaa aggggaacct ataataaatt   7440
actatgaccc tctagtgttt ccttctgatg agtttgatgc atcaatatct caagtcaatg   7500
aaaaaattaa tcaaagttta gcttttattc gtagatccga tgaattatta cataatgtaa   7560
atactggaaa atctactaca aatattatga taactgcaat tattatagta atcattgtag   7620
tattgttatc attaatagct attggtttac tgttgtattg caaagccaaa aacacaccag   7680
ttacactaag caaagaccaa ctaagtggaa tcaataatat tgcattcagc aaatagataa   7740
aaatagcacc taatcatgtt cttacaatgg tttactatct gctcatagac aacccatcta   7800
tcattggatt ttcttaaaat ctgaacttca tcgaaactct tatctataaa ccatctcact   7860
tacactattt aagtagattc ctagtttata gttatataaa acacaattga atgccagtcg   7920
accttaccat ctgtaaaaat gaaaactggg gcaaatatgt cacgaaggaa tccttgcaaa   7980
tttgaaattc gaggtcattg cttaaatggt aagaggtgtc attttagtca taattatttt   8040
gaatggccac cccatgcact gcttgtaaga caaaacttta tgttaaacag aatacttaag   8100
tctatggata aaagtataga taccttatca gaaataagtg gagctgcaga gttggacaga   8160
acagaagagt atgctcttgg tgtagttgga gtgctagaga gttatatagg atcaataaac   8220
aatataacta acaatcagc atgtgttgcc atgagcaaac tcctcactga actcaatagt   8280
gatgatatca aaaagctgag ggacaatgaa gagctaaatt cacccaagat aagagtgtac   8340
aatactgtca tatcatatat tgaaagcaac aggaaaaaca ataaacaaac tatccatctg   8400
ttaaaaagat tgccagcaga cgtattgaag aaaaccatca aaacacatt ggatatccat   8460 aagagcataa ccatcaacaa cccaaaagaa tcaactgtta gtgatacaaa tgaccatgcc   8520
aaaaataatg atactacctg acaaatatcc ttgtagtata acttccatac taataacaag   8580
tagatgtaga gttactatgt ataatcaaaa gaacacacta tatttcaatc aaaacaaccc   8640
aaataaccat atgtactcac cgaatcaaac attcaatgaa atccattgga cctctcaaga   8700
attgattgac acaattcaaa attttctaca acatctaggt attattgagg atatatatac   8760
```

```
aatatatata ttagtgtcat aacactcaat tctaacactc accacatcgt tacattatta    8820
attcaaacaa ttcaagttgt gggacaaaat ggatcccatt attaatgaa attctgctaa    8880 tgtttatcta accgatagtt atttaaaagg tgttatctct ttctcagagt gtaatgcttt    8940
aggaagttac atattcaatg gtccttatct caaaaatgat tataccaact taattagtag    9000
acaaaatcca ttaatagaac acatgaatct aaagaaacta aatataacac agtccttaat    9060
atctaagtat cataaaggtg aaataaaatt agaagaacct acttattttc agtcattact    9120
tatgacatac aagagtatga cctcgtcaga acagattgct accactaatt tacttaaaaa    9180
gataataaga agagctatag aaataagtga tgtcaaagtc tatgctatat tgaataaact    9240
agggcttaaa gaaaaggaca agattaaatc caacaatgga caagatgaag acaactcagt    9300 tattcgacc ataatcaaag atgatatact ttcagctgtt aaagataatc aatctcatct    9360
taaagcagac aaaaatcact ctacaaaaca aaaagacaca atcaaaacaa cactcttgaa    9420
gaaattgatg tgttcaatgc aacatcctcc atcatggtta atacattggt ttaacttata    9480
cacaaaatta aacaacatat taacacagta tcgatcaaat gaggtaaaaa accatgggtt    9540
tacattgata gataatcaaa ctcttagtgg atttcaattt attttgaacc aatatggttg    9600
tatagtttat cataaggaac tcaaaagaat tactgtgaca acctataatc aattcttgac    9660
atggaaagat attagcctta gtagattaaa tgtttgttta attacatgga ttagtaactg    9720
cttgaacaca ttaaataaaa gcttaggctt aagatgcgga ttcaataatg ttatcttgac    9780
acaactattc ctttatggag attgtatact aaagctattt cacaatgagg ggttctacat    9840
aataaaagag gtagagggat ttattatgtc tctaatttta aatataacag aagaagatca    9900
attcagaaaa cgattttata atagtatgct caacaacatc acagatgctg ctaataaagc    9960
tcagaaaaat ctgctatcaa gagtatgtca tacattatta gataagacag tgtccgataa   10020
tataataaat ggcagatgga taattctatt aagtaagttc cttaaattaa ttaagcttgc   10080
aggtgacaat aaccttaaca atctgagtga actatatttt ttgttcagaa tatttggaca   10140
cccaatggta gatgaaagac aagccatgga tgctgttaaa attaattgca atgagaccaa   10200
attttacttg ttaagcagtc tgagtatgtt aagaggtgcc tttatatata gaattataaa   10260
agggtttgta aataattaca acagatggcc tactttaaga aatgctattg ttttaccctt   10320
aagatggtta acttactata aactaaacac ttatccttct tgttggaac ttacagaaag   10380 agatttgatt gtgttatcag gactacgttt ctatcgtgag tttcggttgc ctaaaaaagt   10440
ggatcttgaa atgattataa atgataaagc tatatcacct cctaaaaatt tgatatggac   10500
tagtttccct agaaattaca tgccatcaca catacaaaac tatatagaac atgaaaaatt   10560 aaaatttcc gagagtgata aatcaagaag agtattagag tattatttaa gagataacaa   10620
attcaatgaa tgtgatttat acaactgtgt agttaatcaa agttatctca acaaccctaa   10680
tcatgtggta tcattgacag gcaaagaaag agaactcagt gtaggtagaa tgtttgcaat   10740
gcaaccggga atgttcagac aggttcaaat attggcagag aaaatgatag ctgaaaacat   10800
tttacaattc tttcctgaaa gtcttacaag atatggtgat ctagaactac aaaaaatatt   10860
agaattgaaa gcaggaataa gtaacaaatc aaatcgctac aatgataatt acaacaatta   10920
cattagtaag tgctctatca tcacagatct cagcaaattc aatcaagcat ttcgatatga   10980
aacgtcatgt atttgtagtg atgtgctgga tgaactgcat ggtgtacaat ctctattttc   11040
ctggttacat ttaactattc ctcatgtcac aataatatgc acatataggc atgcacccc   11100
```

```
ctatatagga gatcatattg tagatcttaa caatgtagat gaacaaagtg gattatatag   11160
atatcacatg ggtggcatcg aagggtggtg tcaaaaactg tggaccatag aagctatatc   11220
actattggat ctaatatctc tcaaagggaa attctcaatt actgctttaa ttaatggtga   11280
caatcaatca atagatataa gcaaaccaat cagactcatg gaaggtcaaa ctcatgctca   11340
agcagattat ttgctagcat taaatagcct taaattactg tataaagagt atgcaggcat   11400
aggccacaaa ttaaaaggaa ctgagactta tatatcacga gatatgcaat ttatgagtaa   11460
aacaattcaa cataacggtg tatattaccc agctagtata aagaaagtcc taagagtggg   11520
accgtggata aacactatac ttgatgattt caaagtgagt ctagaatcta taggtagttt   11580
gacacaagaa ttagaatata gaggtgaaag tctattatgc agtttaatat ttagaaatgt   11640
atggttatat aatcagattg ctctacaatt aaaaaatcat gcattatgta acaataaact   11700
atatttggac atattaaagg ttctgaaaca cttaaaaacc ttttttaatc ttgataatat   11760
tgatacagca ttaacattgt atatgaattt acccatgtta tttggtggtg gtgatcccaa   11820
cttgttatat cgaagtttct atagaagaac tcctgacttc ctcacagagg ctatagttca   11880
ctctgtgttc atacttagtt attatacaaa ccatgactta aaagataaac ttcaagatct   11940
gtcagatgat agattgaata agttcttaac atgcataatc acgtttgaca aaaaccctaa   12000
tgctgaattc gtaacattga tgagagatcc tcaagcttta gggtctgaga gacaagctaa   12060
aattactagc gaaatcaata gactggcagt tacagaggtt ttgagtacag ctccaaacaa   12120
aatattctcc aaaagtgcac aacattatac tactacagag atagatctaa atgatattat   12180
gcaaaatata gaacctacat atcctcatgg gctaagagtt gtttatgaaa gtttaccctt   12240
ttataaagca gagaaaatag taaatcttat atcaggtaca aaatctataa ctaacatact   12300
ggaaaaaact tctgccatag acttaacaga tattgataga gccactgaga tgatgaggaa   12360
aaacataact ttgcttataa ggatacttcc attggattgt aacagagata aagagagat   12420 attgagtatg gaaaacctaa gtattactga attaagcaaa tatgttaggg aaagatcttg   12480
gtctttatcc aatatagttg gtgttacatc acccagtatc atgtatacaa tggacatcaa   12540
atatactaca agcactatat ctagtggcat aattatagag aaatataatg ttaacagttt   12600
aacacgtggt gagagaggac ccactaaacc atgggttggt tcatctacac aagagaaaaa   12660
aacaatgcca gttataata gacaagtctt aaccaaaaaa cagagagatc aaatagatct   12720
attagcaaaa ttggattggg tgtatgcatc tatagataac aaggatgaat tcatggaaga   12780
actcagcata ggaaccccttg ggttaacata tgaaaaggcc aagaaattat ttccacaata   12840
tttaagtgtc aattatttgc atcgccttac agtcagtagt agaccatgtg aattccctgc   12900
atcaatacca gcttatagaa caacaaatta tcactttgac actagcccta ttaatcgcat   12960
attaacagaa aagtatggtg atgaagatat tgacatagta ttccaaaact gtataagctt   13020
tggccttagt ttaatgtcag tagtagaaca atttactaat gtatgtccta acagaattat   13080 tctcataccct aagcttaatg agatacattt gatgaaacct cccatattca caggtgatgt   13140
tgatattcac aagttaaaac aagtgataca aaaacagcat atgttttta cagacaaaat   13200 aagtttgact caatatgtgg aattattctt aagtaataaa acactcaaat ctggatctca   13260
tgttaattct aatttaatat tggcacataa aatatctgac tattttcata atacttacat   13320
tttaagtact aatttagctg gacattggat tctgattata caacttatga aagattctaa   13380
aggtattttt gaaaaagatt ggggagaggg atatatacact gatcatatgt ttattaattt   13440
gaaagttttc ttcaatgctt ataagaccta tctcttgtgt tttcataaag gttatggcaa   13500
```

```
agcaaagctg gagtgtgata tgaacacttc agatcttcta tgtgtattgg aattaataga    13560
cagtagttat tggaagtcta tgtctaaggt attttagaa caaaaagtta tcaaatacat    13620
tcttagccaa gatgcaagtt tacatagagt aaaaggatgt catagcttca aattatggtt    13680
tcttaaacgt cttaatgtag cagaattcac agtttgccct tgggttgtta acatagatta    13740
tcatccaaca catatgaaag caatattaac ttatatagat cttgttagaa tgggattgat    13800
aaatatagat agaatacaca ttaaaaataa acacaaattc aatgatgaat tttatacttc    13860
taatctcttc tacattaatt ataacttctc agataatact catctattaa ctaaacatat    13920
aaggattgct aattctgaat tagaaaataa ttacaacaaa ttatatcatc ctacaccaga    13980
aaccctagag aatatactag ccaatccgat taaaagtaat gacaaaaaga cactgaatga    14040
ctattgtata ggtaaaaatg ttgactcaat aatgttacca ttgttatcta ataagaagct    14100
tattaaatcg tctgcaatga ttagaaccaa ttacagcaaa caagatttgt ataatttatt    14160
ccctatggtt gtgattgata gaattataga tcattcaggc aatacagcca aatccaacca    14220
actttacact actacttccc accaaatatc tttagtgcac aatagcacat cactttactg    14280
catgcttcct tggcatcata ttaatagatt caattttgta tttagttcta caggttgtaa    14340
aattagtata gagtatattt taaaagatct taaaattaaa gatcccaatt gtatagcatt    14400
cataggtgaa ggagcaggga atttattatt gcgtacagta gtggaacttc atcctgacat    14460
aagatatatt tacagaagtc tgaaagattg caatgatcat agtttaccta ttgagttttt    14520
aaggctgtac aatggacata tcaacattga ttatggtgaa aatttgacca ttcctgctac    14580
agatgcaacc aacaacattc attggtctta tttacatata aagtttgctg aacctatcag    14640 tcttttttgtc tgtgatgccg aattgtctgt aacagtcaac tggagtaaaa ttataataga    14700
atggagcaag catgtaagaa agtgcaagta ctgttcctca gttaataaat gtatgttaat    14760
agtaaaatat catgctcaag atgatattga tttcaaatta gacaatataa ctatattaaa    14820
aacttatgta tgcttaggca gtaagttaaa gggatcggag gtttacttag tccttacaat    14880
aggtcctgcg aatatattcc cagtatttaa tgtagtacaa aatgctaaat tgatactatc    14940
aagaaccaaa aatttcatca tgcctaagaa agctgataaa gagtctattg atgcaaatat    15000
taaaagtttg ataccctttc tttgttaccc tataacaaaa aaaggaatta atactgcatt    15060
gtcaaaacta aagagtgttg ttagtggaga tatactatca tattctatag ctggacgtaa    15120
tgaagttttc agcaataaac ttataaatca taagcatatg aacatcttaa aatggttcaa    15180
tcatgtttta aatttcagat caacagaact aaactataac catttatata tggtagaatc    15240
tacatatcct tacctaagtg aattgttaaa cagcttgaca accaatgaac ttaaaaaact    15300
gattaaaatc acaggtagtc tgttatacaa ctttcataat gaataatgaa taaagatctt    15360
ataataaaaa ttcccatagc tatacactaa cactgtattc aattatagtt attaaaaatt    15420
aaaaatcgta cgatttttta aataactttt agtgaactaa tcctaaagtt atcattttaa    15480
tcttggagga ataaatttaa accctaatct aattggttta tatgtgtatt aactaaatta    15540
cgagatatta gtttttgaca ctttttttct cgt                                15573
```

CHIMERIC RSV, IMMUNOGENIC COMPOSITIONS, AND METHODS OF USE

CROSS REFERENCE TO RELATED APPLICATIONS

This application is a continuation of U.S. application Ser. No. 15/772,275 filed Apr. 30, 2018, which is a national stage application filed under 35 U.S.C. § 371 of PCT/US2016/058976 filed Oct. 27, 2016, which claims priority to U.S. Provisional Application No. 62/247,962 filed Oct. 29, 2015 and U.S. Provisional Application No. 62/334,547 filed May 11, 2016. The entirety of each of these applications [is] are hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 15198PCT_ST25.txt. The text file is 49 KB, was created on Oct. 26, 2016, and is being submitted electronically via EFS-Web.

REFERENCE TO SEQUENCE LISTING

The sequence listing submitted on Apr. 10, 2023, as an .XML file entitled "10029_055US2_ST25.TXT" created on Sep. 23, 2022, and having a file size of 49,518 bytes is hereby incorporated by reference pursuant to 37 C.F.R. § 1.52(e)(5).

BACKGROUND

Human respiratory syncytial virus (RSV) causes respiratory tract infections. It is the major cause of hospital visits during infancy and childhood. Palivizumab is a humanized monoclonal antibody (IgG) that binds the RSV fusion protein (RSV F) that is FDA approved for prevention of serious lower respiratory tract disease caused by RSV in certain high-risk infants. Palivizumab, as chimeric antibody administered in monthly doses, has limited efficacy and sometimes causes allergic reactions. Thus, there is a need to identify improved treatment and prevention methods for RSV.

Vaccines are typically killed (inactivated) or weakened (attenuated) versions of a live viral strain. Kim et al. report that administration of a formalin-inactivated RSV vaccine was not sufficiently effective. Am J Epidemiol 89, 422-434 (1969). Attenuated RSV vaccine candidates face significant safety hurdles, and the development of pediatric RSV live-attenuated vaccine (LAV) strains that are sufficiently attenuated and immunogenic have been elusive. See Collins et al. Progress in understanding and controlling respiratory syncytial virus: still crazy after all these years. Virus Res 162, 80-99 (2011).

Karron et al. report RSV where most of the open reading frame (ORF) of the RNA synthesis factor M2-2 was deleted yields an attenuated RSV vaccine with improved antibody responses in children. Sci Transl Med 7, 312ra175 (2015). Meng, et al. report attenuation and immunogenicity of respiratory syncytial virus by targeted codon deoptimization of virulence genes. MBio 5, e01704-01714 (2014). See also U.S. Published Application number 2016/0030549. Hotard et al. report residues in the human RSV fusion protein that modulate fusion activity and pathogenesis, 2015, J Virol 89:512-522. Rostad et al. report a recombinant respiratory syncytial virus vaccine candidate attenuated by a low-fusion F protein is immunogenic and protective against challenge in cotton rats. J Virol, 2016, 90 (16): 7508-7518.

References cited herein are not an admission of prior art.

SUMMARY

This disclosure relates to chimeric respiratory syncytial virus (RSV), live attenuated vaccine and immunogenic compositions, and methods of use. In certain embodiments, the chimeric RSV has a mutated gene pattern encoding an RSV F protein having M at position 79, R at position 191, K at position 357, and/or Y at position 371. In certain embodiments, the RSV F protein has V at position 557 or the F protein is mutated such that position 557 is V.

In certain embodiments, M at position 79, R at position 191, K at position 357, and Y at position 371 are not in an RSV F protein wherein the naturally occurring RSV F protein has that particular pattern of amino acids, i.e., the mutant RSV F protein comprises at least one amino acid substitution such that the mutated RSF F protein has at least one modification at position 79, 191, 357 or 371 when compared to the naturally occurring sequence to provide an RSV F protein pattern of amino acids having M at position 79, R at position 191, K at position 357, and Y at position 371.

In certain embodiment the RSV F protein that is mutated is derived from an RSV F protein other than the F protein found in RSV line 19 such as an RSV strain of subgroup B, e.g., a "Buenos Aires" (BAF) strain. In certain embodiments, the RSV F protein does not contain SEQ ID NO: 3 or 4 or does not have substantial identity to SEQ ID NO: 3 or 4. In certain embodiments, the mutated RSV F has more than 85% or 90% identity to SEQ ID NO: 1 but less than 95%, 96%, 97%, 98%, or 99% identity to SEQ ID NO: 4. In certain embodiments, the mutated RSV F has more than 85% identity to SEQ ID NO: 1 but less than 99% identity to SEQ ID NO: 4.

In certain embodiments, the RSV F protein that is mutated has (SEQ ID NO: 1)
MELLIHRSSAIFLTLAINALYLTSSQNITEEFYQSTCSAVARGYLSALRTGWYTSVITIELS

NIKETKCNGTDTKVKLMKQELDKYKNAVTELQLLMQNTPAANNRARREAPQYMNYTI

NTTKNLNVSISKKRKRRFLGFLLGVGSAIASGIAVSKVLHLEGEVNKIKNALLSTNKAVV

SLSNGVSVLTSRVLDLKNYINNQLLPIVNQQSCRISNIETVIEFQQKNSRLLEITREFSVNA

GVTTPLSTYMLTNSELLSLINDMPITNDQKKLMSSNVQIVRQQSYSIMSIIKEEVLAYVVQ

```
LPIYGVIDTPCWKLHTSPLCTTNIKEGSNICLTRTDRGWYCDNAGSVSFFPQADKCKVQS

NRVFCDTMYSLTLPSEVSLCNTDIFNSKYDCKIMTSKTDISSSVITSLGAIVSCYGKTKCT

ASNKNRGIIKTFSNGCDYVSNKGVDTVSVGNTLYYVNKLEGKNLYVKGEPIINYYDPLV

FPSDEFDASISQVNEKINQSLAFIRRSDELLHNVNTGKSTTNIMITAIIIVIIVVLLSLIAIGLL

LYCKAKNTPVTLSKDQLSGINNIAFS,
``` or variants thereof.

In certain embodiments, this disclosure contemplates a chimeric RSV F protein lacking the transmembrane domain, or having amino acids 1-524, e.g.,

```
                                                    (SEQ ID NO: 13)
MELLIHRSSAIFLTLAINALYLTSSQNITEEFYQSTCSAVSRGYLSALRTGWYTSVITIELS

NIKETKCNGTDTKVKLMKQELDKYKNAVTELQLLMQNTPAANNRARREAPQYMNYTI

NTTKNLNVSISKKRKRRFLGFLLGVGSAIASGIAVSKVLHLEGEVNKIKNALLSTNKAVV

SLSNGVSVLTSRVLDLKNYINNQLLPIVNQQSCRISNIETVIEFQQKNSRLLEITREFSVNA

GVTTPLSTYMLTNSELLSLINDMPITNDQKKLMSSNVQIVRQQSYSIMSIIKEEVLAYVVQ

LPIYGVIDTPCWKLHTSPLCTTNIKEGSNICLTRTDRGWYCDNAGSVSFFPQADKCKVQS

NRVFCDTMYSLTLPSEVSLCNTDIFNSKYDCKIMTSKTDISSSVITSLGAIVSCYGKTKCT

ASNKNRGIIKTFSNGCDYVSNKGVDTVSVGNTLYYVNKLEGKNLYVKGEPIINYYDPLV

FPSDEFDASISQVNEKINQSLAFIRRSDELLHNVNTGKSTTN.
```

In certain embodiments, the variant has greater than 95%, 98%, or 99% sequence identity or similarity to SEQ ID NO: 1. In certain embodiments, the variants are one, two, three, or more amino acid substitutions, deletions, or insertions provided that there are not any substitutions of M at position 79, R at position 191, K at position 357, or Y at position 371. In certain embodiments, substitutions are conserved substitutions.

In certain embodiment, an RSV F variant has a V at position 11, has F at position 20, has an A at position 23, has F at position 45, has a T or V at position 102, has a V at position 103, has a V at position 119, has an A at position 121, has an R at position 123, has an S at position 104, has a T at position 129, has an A at position 173, has an R a position 242, has an N at position 276, has an A as position 518, has a V at position 529, has a T at position 554, or combinations thereof.

In certain embodiments, the variants of RSV F protein sequences disclosed herein have one, two, three, or more amino acid substitutions, deletions, or insertions provided that there are not any substitutions of M at position 79, R at position 191, K at position 357, or Y at position 371. In certain embodiments, substitutions are conserved substitutions.

In certain embodiments, the variants are one or two more amino acid substitutions, deletions, or insertions, provided the substitutions are not any substitutions of M at position 79, R at position 191, K at position 357, Y at position 371, and V at position 557. In certain embodiments, substitutions are conserved substitutions.

In certain embodiments, the variants are one, two, or three amino acid substitutions, deletions, or insertions provided the substitutions are not any substitutions of M at position 79, R at position 191, K at position 357, or Y at position 371. In certain embodiments, substitutions are conserved substitutions.

In certain embodiments, the variants are one, two, or three amino acid substitutions, deletions, or insertions, provided the substitutions are not any substitutions of M at position 79, R at position 191, K at position 357, Y at position 371, and V at position 557. In certain embodiments, substitutions are conserved substitutions.

In certain embodiments, the variants do not contain more than 4, 5, 6, 7, 8, 9, 10 or 20 amino acid substitutions, deletions, or insertions, provided the substitutions are not any substitutions of M at position 79, R at position 191, K at position 357, and Y at position 371. In certain embodiments, substitutions are conserved substitutions.

In certain embodiments, the variants do not contain more than 4, 5, 6, 7, 8, 9, 10 or 20 amino acid substitutions, deletions, or insertions, provided the substitutions are not any substitutions of M at position 79, R at position 191, K at position 357, Y at position 371, and V at position 557. In certain embodiments, substitutions are conserved substitutions.

In certain embodiments, the chimeric RSV has genes encoding RSV NS1, NS2, and G proteins are codon-deoptimized such that the rate of expression of NS1, NS2, and G is reduced by more than half in Vero cells compared to the wild type A2 virus.

In certain embodiments, the rate of expression of G in mammalian cells is reduce by more than one third (⅓), one fourth, (¼), one fifth (⅕), or one tenth (⅒) in Vero cells compared to the wild type A2 virus.

In certain embodiments, the rate of expression of NS1 is reduce by more than one third (⅓), one fourth, (¼), one fifth (⅕), or one tenth (⅒) in Vero cells compared to the wild type line A2 virus.

In certain embodiments, the rate of expression of NS2 is reduce by more than one third (⅓), one fourth, (¼), one fifth (⅕), or one tenth (⅒) in Vero cells compared to the wild type line A2 virus.

In certain embodiments, the gene encoding the SH protein is deleted or altered such that a truncated protein or no protein is expressed. In certain embodiments, the gene encoding the M2-2 is deleted or altered such that a truncated protein or no protein is expressed.

In certain embodiments, the gene encoding F protein is mutated such that position 557 is not V or that I is in position 557.

In certain embodiments, the disclosure contemplates fusion proteins comprising RSV F proteins disclosed herein, e.g., SEQ ID NO: 1, 13, and variants.

In certain embodiments, this disclosure relates to vaccine and immunogenic compositions comprising chimeric RSV disclosed herein. In certain embodiments, the compositions further comprise an adjuvant and/or other pharmaceutically acceptable carrier. In certain embodiments, the adjuvant is an aluminum gel, aluminum salt, or monophosphoryl lipid A.

In certain embodiments, the adjuvant is an oil-in-water emulsion. In certain embodiments, the oil-in-water emulsion further comprises a-tocopherol, squalene, and/or a surfactant.

In certain embodiments, the disclosure relates to methods for vaccinating or immunizing a subject against respiratory syncytial virus, the method comprising administering to the subject an effective amount of a chimeric RSV disclosed herein or immunogenic composition comprising the same. In certain embodiments, the effective amount produces a protective immune response in the subject.

In certain embodiments, the subject is a pregnant mother, a child under 2, 3, or 4 years old. In certain embodiments, subject has a reduced immune system, is over 60 or 65 years old or is regularly administered a chemotherapy or immune suppressive medication.

In certain embodiments, the disclosure relates to nucleic acids encoding an RSV F proteins disclosed herein. In certain embodiments, the nucleic acid comprises

```
                                                          SEQ ID NO: 14
ATGGAGTTGCTGATCCATAGATCAAGTGCAATCTTCCTAACTCTTGCTATTAA

TGCATTGTACCTCACCTCAAGTCAGAACATAACTGAGGAGTTTTACCAATCGACATG

TAGTGCAGTTAGCAGAGGTTACTTGAGTGCTTTAAGAACAGGTTGGTATACCAGTGT

CATAACAATAGAATTAAGTAATATAAAAGAAACCAAATGCAATGGAACTGACACTA

AAGTAAAACTTATAAAACAAGAATTAGATAAGTATAAGAATGCAGTAACAGAATTA

CAGTTACTTATGCAAAACACACCAGCTGCCAACAACCGGGCCAGAAGAGAAGCACC

ACAGTATATGAACTACACAATCAATACCACTAAAAACCTAAATGTATCAATAAGCA

AGAAGAGGAAACGAAGATTTCTGGGCTTCTTGTTAGGTGTAGGATCTGCAATAGCA

AGTGGTATAGCTGTATCCAAAGTTCTACACCTTGAAGGAGAAGTGAACAAGATCAA

AAATGCTTTGCTGTCTACAAACAAAGCTGTAGTCAGTCTATCAAATGGGGTCAGTGT

TTTAACCAGCAAAGTGTTAGATCTCAAGAATTATATAAACAACCAATTATTACCTAT

AGTAAATCAACAGAGTTGTCGCATTTCCAACATTGAAACAGTTATAGAATTCCAGCA

GAAGAACAGCAGATTGTTGGAAATCACCAGAGAATTTAGTGTCAATGCAGGTGTAA

CGACACCTTTAAGCACTTACATGTTAACAAACAGTGAGTTACTATCATTAATCAATG

ATATGCCTATAACAAATGATCAGAAAAAATTAATGTCAAGCAATGTTCAGATAGTA

AGGCAACAAAGTTATTCTATCATGTCTATAATAAAGGAAGAAGTCCTTGCATATGTT

GTACAGCTACCTATCTATGGTGTAATTGATACACCTTGCTGGAAATTACACACATCA

CCTCTGTGCACCACCAACATCAAAGAAGGATCAAATATTTGTTTAACAAGGACTGAT

AGAGGATGGTACTGTGATAATGCAGGATCAGTATCCTTCTTTCCACAGGCTGACACT

TGTAAAGTACAGTCCAATCGAGTATTTTGTGACACTATGAACAGTTTGACATTACCA

AGTGAAGTCAGCCTTTGTAACACTGACATATTCAATTCCAAGTATGACTGCAAAATT

ATGACATCAAAAACAGACATAAGCAGCTCAGTAATTACTTCTCTAGGAGCTATAGTG

TCATGCTATGGTAAAACTAAATGCACTGCATCCAACAAAAATCGTGGAATTATAAA

GACATTTTCTAATGGTTGTGATTATGTGTCAAACAAAGGAGTAGATACTGTATCAGT

GGGCAACACTTTATACTATGTCAACAAGCTGGAAGGCAAAAACCTTTATGTAAAAG

GGGAACCTATAATAAATTACTATGACCCTCTAGTGTTTCCTTCTGATGAGTTTGATGC

ATCAATATCTCAAGTCAATGAAAAAATTAATCAAAGTTTAGCTTTTATTCGTAGATC
```

-continued

```
CGATGAATTATTACATAATGTAAATACTGGAAAATCTACTACAAATATTATGATAAC

TGCAATTATTATAGTAATCATTGTAGTATTGTTATCATTAATAGCTATTGGTTTACTG

TTGTATTGCAAAGCCAAAAACACACCAGTTACACTAAGCAAAGACCAACTAAGTGG

AATCAATAATATTGCATTCAGCAAATAG,
``` or a variants with greater than 50, 60, 70, 80, 90, 95, 98, or 99% sequence identity.

In certain embodiments, the disclosure relates to vectors comprising a nucleic acid encoding an RSV F proteins disclosed herein. In certain embodiments, the vector is selected from a plasmid or a bacterial artificial chromosome.

In certain embodiments, chimeric RSV comprises

SEQ ID NO: 15
```
ACGCGAAAAAATGCGTACAACAAACTTGCATAAACCAAAAAAATGGGGCAA

ATAAGAATTTGATAAGTACCACTTAAATTTAACTCCCTTGCTTAGCGATGGTGAGCG

AGCTGATTAAGGAGAACATGCACATGAAGCTGTACATGGAGGGCACCGTGAACAAC

CACCACTTCAAGTGCACATCCGAGGGCGAAGGCAAGCCCTACGAGGGCACCCAGAC

CATGAGAATCAAGGCGGTCGAGGGCGGCCCTCTCCCCTTCGCCTTCGACATCCTGGC

TACCAGCTTCATGTACGGCAGCAAAACCTTCATCAACCACACCCAGGGCATCCCCGA

CTTCTTTAAGCAGTCCTTCCCCGAGGGCTTCACATGGGAGAGAGTCACCACATACGA

AGACGGGGCGTGCTGACCGCTACCCAGGACACCAGCCTCCAGGACGGCTGCCTCA

TCTACAACGTCAAGATCAGAGGGGTGAACTTCCCATCCAACGGCCCTGTGATGCAG

AAGAAAACACTCGGCTGGGAGGCCTCCACCGAGACCCTGTACCCCGCTGACGGCGG

CCTGGAAGGCAGAGCCGACATGGCCCTGAAGCTCGTGGGCGGGGCCACCTGATCT

GCAACTTGAAGACCACATACAGATCCAAGAAACCCGCTAAGAACCTCAAGATGCCC

GGCGTCTACTATGTGGACAGAAGACTGGAAAGAATCAAGGAGGCCGACAAAGAGA

CCTACGTCGAGCAGCACGAGGTGGCTGTGGCCAGATACTGCGACCTCCCTAGCAAA

CTGGGGCACAGATGAGTATTCAATTATAGTTATTAAAAACTTAACAGAAGACAAAA

ATGGGGCAAATAAGAATTTGATAAGTACCACTTAAATTTAACTCCCTTGCTTAGCGA

TGGGTTCGAATTCGCTATCGATGATAAAAGTACGTCTACAAAATCTATTTGATAATG

ATGAAGTAGCGCTACTAAAAATAACGTGTTATACGGATAAACTAATACATCTAACG

AATGCGCTAGCGAAAGCGGTAATACATACGATAAAACTAAATGGTATAGTATTTGT

ACATGTAATAACGTCGTCGGATATATGTCCGAATAATAATATAGTAGTAAAATCGAA

TTTTACGACGATGCCGGTACTACAAAATGGTGGTTATATATGGGAAATGATGGAACT

AACGCATTGTTCGCAACCGAATGGTCTACTAGATGATAATTGTGAAATAAAATTTTC

GAAAAAACTATCGGATTCGACGATGACGAATTATATGAATCAACTATCGGAACTAC

TAGGTTTTGATCTAAATCCGTAAATTATAATTAATATCAACTAGCAAATCAATGTCA

CTAACACCATTAGTTAATATAAAACTTAACAGAAGACAAAAATGGGGCAAATAAAT

CAATTCAGCCAACCCAACCATGGATACGACGCATAATGATAATACGCCGCAACGTC

TAATGATAACGGATATGCGTCCGCTATCGCTAGAAACGATAATAACGTCGCTAACGC

GTGATATAATAACGCATAAATTTATATATCTAATAAATCATGAATGTATAGTACGTA

AACTAGATGAACGTCAAGCGACGTTTACGTTTCTAGTAAATTATGAAATGAAACTAC

TACATAAAGTAGGTTCGACGAAATATAAAAAATATACGGAATATAATACGAAATAT

GGTACGTTTCCGATGCCGATATTTATAAATCATGATGGTTTTCTAGAATGTATAGGT

ATAAAACCGACGAAACATACGCCGATAATATATAAATATGATCTAAATCCGTAAAT
```

-continued

```
TTCAACACAATATTCACACAATCTAAAACAACAACTCTATGCATAACTATACTCCAT
AGTCCAGATGGAGCCTGAAAATTATAGTAATTTAAAATTAAGGAGAGATATAAGAT
AGAAGATGGGGCAAATACAAAGATGGCTCTTAGCAAAGTCAAGTTGAATGATACAC
TCAACAAAGATCAACTTCTGTCATCCAGCAAATACACCATCCAACGGAGCACAGGA
GATAGTATTGATACTCCTAATTATGATGTGCAGAAACACATCAATAAGTTATGTGGC
ATGTTATTAATCACAGAAGATGCTAATCATAAATTCACTGGGTTAATAGGTATGTTA
TATGCGATGTCTAGGTTAGGAAGAGAAGACACCATAAAAATACTCAGAGATGCGGG
ATATCATGTAAAAGCAAATGGAGTAGATGTAACAACACATCGTCAAGACATTAATG
GAAAAGAAATGAAATTTGAAGTGTTAACATTGGCAAGCTTAACAACTGAAATTCAA
ATCAACATTGAGATAGAATCTAGAAAATCCTACAAAAAAATGCTAAAAGAAATGGG
AGAGGTAGCTCCAGAATACAGGCATGACTCTCCTGATTGTGGGATGATAATATTATG
TATAGCAGCATTAGTAATAACTAAATTAGCAGCAGGGGACAGATCTGGTCTTACAG
CCGTGATTAGGAGAGCTAATAATGTCCTAAAAAATGAAATGAAACGTTACAAAGGC
TTACTACCCAAGGACATAGCCAACAGCTTCTATGAAGTGTTTGAAAAACATCCCCAC
TTTATAGATGTTTTTGTTCATTTTGGTATAGCACAATCTTCTACCAGAGGTGGCAGTA
GAGTTGAAGGGATTTTTGCAGGATTGTTTATGAATGCCTATGGTGCAGGGCAAGTGA
TGTTACGGTGGGAGTCTTAGCAAAATCAGTTAAAAATATTATGTTAGGACATGCTA
GTGTGCAAGCAGAAATGGAACAAGTTGTTGAGGTTTATGAATATGCCCAAAAATTG
GGTGGTGAAGCAGGATTCTACCATATATTGAACAACCCAAAAGCATCATTATTATCT
TTGACTCAATTTCCTCACTTCTCCAGTGTAGTATTAGGCAATGCTGCTGGCCTAGGCA
TAATGGGAGAGTACAGAGGTACACCGAGGAATCAAGATCTATATGATGCAGCAAAG
GCATATGCTGAACAACTCAAAGAAATGGTGTGATTAACTACAGTGTACTAGACTTG
ACAGCAGAAGAACTAGAGGCTATCAAACATCAGCTTAATCCAAAAGATAATGATGT
AGAGCTTTGAGTTAATAAAAAATGGGGCAAATAAATCATCATGGAAAAGTTTGCTC
CTGAATTCCATGGAGAAGATGCAAACAACAGGGCTACTAAATTCCTAGAATCAATA
AAGGGCAAATTCACATCACCCAAAGATCCCAAGAAAAAAGATAGTATCATATCTGT
CAACTCAATAGATATAGAAGTAACCAAAGAAAGCCCTATAACATCAAATTCAACTA
TTATCAACCCAACAAATGAGACAGATGATACTGCAGGGAACAAGCCCAATTATCAA
AGAAAACCTCTAGTAAGTTTCAAAGAAGACCCTACACCAAGTGATAATCCCTTTTCT
AAACTATACAAAGAAACCATAGAAACATTTGATAACAATGAAGAAGAATCCAGCTA
TTCATACGAAGAAATAAATGATCAGACAAACGATAATATAACAGCAAGATTAGATA
GGATTGATGAAAAATTAAGTGAAATACTAGGAATGCTTCACACATTAGTAGTGGCA
AGTGCAGGACCTACATCTGCTCGGGATGGTATAAGAGATGCCATGATTGGTTTAAGA
GAAGAAATGATAGAAAAAATCAGAACTGAAGCATTAATGACCAATGACAGATTAGA
AGCTATGGCAAGACTCAGGAATGAGGAAAGTGAAAAGATGGCAAAAGACACATCA
GATGAAGTGTCTCTCAATCCAACATCAGAGAAATTGAACAACCTATTGGAAGGGAA
TGATAGTGACAATGATCTATCACTTGAAGATTTCTGATTAGTTACCACTCTTCACATC
AACACACAATACCAACAGAAGACCAACAAACTAACCAACCCAATCATCCAACCAAA
CATCCATCCGCCAATCAGCCAAACAGCCAACAAAACAACCAGCCAATCCAAAACTA
ACCACCCGGAAAAAATCTATAATATAGTTACAAAAAAAGGAAAGGGTGGGGCAAAT
ATGGAAACATACGTGAACAAGCTTCACGAAGGCTCCACATACACAGCTGCTGTTCA
```

-continued

```
ATACAATGTCTTAGAAAAAGACGATGACCCTGCATCACTTACAATATGGGTGCCCAT

GTTCCAATCATCTATGCCAGCAGATTTACTTATAAAAGAACTAGCTAATGTCAACAT

ACTAGTGAAACAAATATCCACACCCAAGGGACCTTCACTAAGAGTCATGATAAACT

CAAGAAGTGCAGTGCTAGCACAAATGCCCAGCAAATTTACCATATGCGCTAATGTGT

CCTTGGATGAAAGAAGCAAACTAGCATATGATGTAACCACACCCTGTGAAATCAAG

GCATGTAGTCTAACATGCCTAAAATCAAAAAATATGTTGACTACAGTTAAAGATCTC

ACTATGAAGACACTCAACCCTACACATGATATTATTGCTTTATGTGAATTTGAAAAC

ATAGTAACATCAAAAAAAGTCATAATACCAACATACCTAAGATCCATCAGTGTCAG

AAATAAAGATCTGAACACACTTGAAAATATAACAACCACTGAATTCAAAAATGCTA

TCACAAATGCAAAAATCATCCCTTACTCAGGATTACTATTAGTCATCACAGTGACTG

ACAACAAAGGAGCATTCAAATACATAAAGCCACAAAGTCAATTCATAGTAGATCTT

GGAGCTTACCTAGAAAAGAAAGTATATATTATGTTACCACAAATTGGAAGCACAC

AGCTACACGATTTGCAATCAAACCCATGGAAGATTAACCTTTTTCCTCTACATCAGT

GTGTTAATTCATACAAACTTTCTACCTACATTCTTCACTTCACCATCACAATCACAAA

CACTCTGTGGTTCAACCAATCAAACAAAACTTATCTGAAGTCCCAGATCATCCCAAG

TCATTGTTTATCAGATCTAGTACTCAAATAAGTTAATAAAAAATATACACATGGACG

TCCATGGGCAAATGCAAACATGTCCAAAAACAAGGACCAACGCACCGCTAAGACA

TTAGAAAGGACCTGGGACACTCTCAATCATTTATTATTCATATCATCGTGCTTATATA

AGTTAAATCTTAAATCTGTAGCACAAATCACATTATCCATTCTGGCAATGATAATCT

CAACTTCACTTATAATTGCAGCCATCATATTCATAGCCTCGGCAAACCACAAAGTCA

CACCAACAACTGCAATCATACAAGATGCAACAAGCCAGATCAAGAACACAACCCCA

ACATACCTCACCCAGAATCCTCAGCTTGGAATCAGTCCCTCTAATCCGTCTGAAATT

ACATCACAAATCACCACCATACTAGCTTCAACAACACCAGGAGTCAAGTCAACCCT

GCAATCCACAACAGTCAAGACCAAAAACACAACAACAACTCAAACACAACCCAGC

AAGCCCACCACAAAACAACGCCAAAACAAACCACCAAGCAAACCCAATAATGATTT

TCACTTTGAAGTGTTCAACTTTGTACCCTGCAGCATATGCAGCAACAATCCAACCTG

CTGGGCTATCTGCAAAAGAATACCAAACAAAAAACCAGGAAAGAAAACCACTACC

AAGCCCACAAAAAAACCAACCCTCAAGACAACCAAAAAAGATCCCAAACCTCAAA

CCACTAAATCAAAGGAAGTACCCACCACCAAGCCCACAGAAGAGCCAACCATCAAC

ACCACCAAAACAAACATCATAACTACACTACTCACCTCCAACACCACAGGAAATCC

AGAACTCACAAGTCAAATGGAAACCTTCCACTCAACTTCCTCCGAAGGCAATCCAA

GCCCTTCTCAAGTCTCTACAACATCCGAGTACCCATCACAACCTTCATCTCCACCCA

ACACACCACGCCAGTAGTTACTTAAAAACATATTATCACAAAAGGCCTTGACCAAC

CGCGGAGAATCAAAATAAACTCTGGGCAAATAACAATGGAGTTGCTGATCCATAG

ATCAAGTGCAATCTTCCTAACTCTTGCTATTAATGCATTGTACCTCACCTCAAGTCAG

AACATAACTGAGGAGTTTTACCAATCGACATGTAGTGCAGTTAGCAGAGGTTACTTG

AGTGCTTTAAGAACAGGTTGGTATACCAGTGTCATAACAATAGAATTAAGTAATATA

AAAGAAACCAAATGCAATGGAACTGACACTAAAGTAAAACTTATAAAACAAGAATT

AGATAAGTATAAGAATGCAGTAACAGAATTACAGTTACTTATGCAAAACACACCAG

CTGCCAACAACCGGGCCAGAAGAGAAGCACCACAGTATATGAACTACACAATCAAT
```

-continued

```
ACCACTAAAAACCTAAATGTATCAATAAGCAAGAAGAGGAAACGAAGATTTCTGGG

CTTCTTGTTAGGTGTAGGATCTGCAATAGCAAGTGGTATAGCTGTATCCAAAGTTCT

ACACCTTGAAGGAGAAGTGAACAAGATCAAAAATGCTTTGCTGTCTACAAACAAAG

CTGTAGTCAGTCTATCAAATGGGGTCAGTGTTTTAACCAGCAAAGTGTTAGATCTCA

AGAATTATATAAACAACCAATTATTACCTATAGTAAATCAACAGAGTTGTCGCATTT

CCAACATTGAAACAGTTATAGAATTCCAGCAGAAGAACAGCAGATTGTTGGAAATC

ACCAGAGAATTTAGTGTCAATGCAGGTGTAACGACACCTTTAAGCACTTACATGTTA

ACAAACAGTGAGTTACTATCATTAATCAATGATATGCCTATAACAAATGATCAGAAA

AAATTAATGTCAAGCAATGTTCAGATAGTAAGGCAACAAAGTTATTCTATCATGTCT

ATAATAAAGGAAGAAGTCCTTGCATATGTTGTACAGCTACCTATCTATGGTGTAATT

GATACACCTTGCTGGAAATTACACACATCACCTCTGTGCACCACCAACATCAAAGAA

GGATCAAATATTTGTTTAACAAGGACTGATAGAGGATGGTACTGTGATAATGCAGG

ATCAGTATCCTTCTTTCCACAGGCTGACACTTGTAAAGTACAGTCCAATCGAGTATTT

TGTGACACTATGAACAGTTTGACATTACCAAGTGAAGTCAGCCTTTGTAACACTGAC

ATATTCAATTCCAAGTATGACTGCAAAATTATGACATCAAAAACAGACATAAGCAG

CTCAGTAATTACTTCTCTAGGAGCTATAGTGTCATGCTATGGTAAAACTAAATGCAC

TGCATCCAACAAAAATCGTGGAATTATAAAGACATTTTCTAATGGTTGTGATTATGT

GTCAAACAAAGGAGTAGATACTGTATCAGTGGGCAACACTTTATACTATGTCAACA

AGCTGGAAGGCAAAAACCTTTATGTAAAAGGGGAACCTATAATAAATTACTATGAC

CCTCTAGTGTTTCCTTCTGATGAGTTTGATGCATCAATATCTCAAGTCAATGAAAAA

ATTAATCAAAGTTTAGCTTTTATTCGTAGATCCGATGAATTATTACATAATGTAAATA

CTGGAAAATCTACTACAAATATTATGATAACTGCAATTATTATAGTAATCATTGTAG

TATTGTTATCATTAATAGCTATTGGTTTACTGTTGTATTGCAAAGCCAAAAACACACC

AGTTACACTAAGCAAAGACCAACTAAGTGGAATCAATAATATTGCATTCAGCAAAT

AGATAAAAATAGCACCTAATCATGTTCTTACAATGGTTTACTATCTGCTCATAGACA

ACCCATCTATCATTGGATTTTCTTAAAATCTGAACTTCATCGAAACTCTTATCTATAA

ACCATCTCACTTACACTATTTAAGTAGATTCCTAGTTTATAGTTATATAAAACACAAT

TGAATGCCAGTCGACCTTACCATCTGTAAAAATGAAAACTGGGGCAAATATGTCAC

GAAGGAATCCTTGCAAATTTGAAATTCGAGGTCATTGCTTAAATGGTAAGAGGTGTC

ATTTTAGTCATAATTATTTTGAATGGCCACCCCATGCACTGCTTGTAAGACAAAACTT

TATGTTAAACAGAATACTTAAGTCTATGGATAAAAGTATAGATACCTTATCAGAAAT

AAGTGGAGCTGCAGAGTTGGACAGAACAGAAGAGTATGCTCTTGGTGTAGTTGGAG

TGCTAGAGAGTTATATAGGATCAATAAACAATATAACTAAACAATCAGCATGTGTTG

CCATGAGCAAACTCCTCACTGAACTCAATAGTGATGATATCAAAAAGCTGAGGGAC

AATGAAGAGCTAAATTCACCCAAGATAAGAGTGTACAATACTGTCATATCATATATT

GAAAGCAACAGGAAAAACAATAAACAAACTATCCATCTGTTAAAAAGATTGCCAGC

AGACGTATTGAAGAAACCATCAAAAACACATTGGATATCCATAAGAGCATAACCA

TCAACAACCCAAAAGAATCAACTGTTAGTGATACAAATGACCATGCCAAAAATAAT

GATACTACCTGACAAATATCCTTGTAGTATAACTTCCATACTAATAACAAGTAGATG

TAGAGTTACTATGTATAATCAAAAGAACACACTATATTTCAATCAAAACAACCCAAA

TAACCATATGTACTCACCGAATCAAACATTCAATGAAATCCATTGGACCTCTCAAGA
```

-continued

```
ATTGATTGACACAATTCAAAATTTTCTACAACATCTAGGTATTATTGAGGATATATA
TACAATATATATATTAGTGTCATAACACTCAATTCTAACACTCACCACATCGTTACAT
TATTAATTCAAACAATTCAAGTIGTGGGACAAAATGGATCCCATTATTAATGGAAAT
TCTGCTAATGTTTATCTAACCGATAGTTATTTAAAAGGTGTTATCTCTTTCTCAGAGT
GTAATGCTTTAGGAAGTTACATATTCAATGGTCCTTATCTCAAAAATGATTATACCA
ACTTAATTAGTAGACAAAATCCATTAATAGAACACATGAATCTAAAGAAACTAAAT
ATAACACAGTCCTTAATATCTAAGTATCATAAAGGTGAAATAAAATTAGAAGAACC
TACTTATTTTCAGTCATTACTTATGACATACAAGAGTATGACCTCGTCAGAACAGAT
TGCTACCACTAATTTACTTAAAAAGATAATAAGAAGAGCTATAGAAATAAGTGATG
TCAAAGTCTATGCTATATTGAATAAACTAGGGCTTAAAGAAAAGGACAAGATTAAA
TCCAACAATGGACAAGATGAAGACAACTCAGTTATTACGACCATAATCAAAGATGA
TATACTTTCAGCTGTTAAAGATAATCAATCTCATCTTAAAGCAGACAAAAATCACTC
TACAAAACAAAAAGACACAATCAAAACAACACTCTTGAAGAAATTGATGTGTTCAA
TGCAACATCCTCCATCATGGTTAATACATTGGTTTAACTTATACACAAAATTAAACA
ACATATTAACACAGTATCGATCAAATGAGGTAAAAAACCATGGGTTTACATTGATA
GATAATCAAACTCTTAGTGGATTTCAATTTATTTTGAACCAATATGGTTGTATAGTTT
ATCATAAGGAACTCAAAAGAATTACTGTGACAACCTATAATCAATTCTTGACATGGA
AAGATATTAGCCTTAGTAGATTAAATGTTTGTTTAATTACATGGATTAGTAACTGCTT
GAACACATTAAATAAAAGCTTAGGCTTAAGATGCGGATTCAATAATGTTATCTTGAC
ACAACTATTCCTTTATGGAGATTGTATACTAAAGCTATTTCACAATGAGGGGTTCTA
CATAATAAAAGAGGTAGAGGGATTTATTATGTCTCTAATTTTAAATATAACAGAAGA
AGATCAATTCAGAAAACGATTTTATAATAGTATGCTCAACAACATCACAGATGCTGC
TAATAAAGCTCAGAAAAATCTGCTATCAAGAGTATGTCATACATTATTAGATAAGAC
AGTGTCCGATAATATAATAAATGGCAGATGGATAATTCTATTAAGTAAGTTCCTTAA
ATTAATTAAGCTTGCAGGTGACAATAACCTTAACAATCTGAGTGAACTATATTTTTT
GTTCAGAATATTTGGACACCCAATGGTAGATGAAAGACAAGCCATGGATGCTGTTA
AAATTAATTGCAATGAGACCAAATTTTACTTGTTAAGCAGTCTGAGTATGTTAAGAG
GTGCCTTTATATATAGAATTATAAAAGGGTTTGTAAATAATTACAACAGATGGCCTA
CTTTAAGAAATGCTATTGTTTTACCCTTAAGATGGTTAACTTACTATAAACTAAACAC
TTATCCTTCTTTGTTGGAACTTACAGAAAGAGATTTGATTGTGTTATCAGGACTACGT
TTCTATCGTGAGTTTCGGTTGCCTAAAAAAGTGGATCTTGAAATGATTATAAATGAT
AAAGCTATATCACCTCCTAAAAATTTGATATGGACTAGTTTCCCTAGAAATTACATG
CCATCACACATACAAAACTATATAGAACATGAAAAATTAAAATTTTCCGAGAGTGA
TAAATCAAGAAGAGTATTAGAGTATTATTTAAGAGATAACAAATTCAATGAATGTG
ATTTATACAACTGTGTAGTTAATCAAAGTTATCTCAACAACCCTAATCATGTGGTAT
CATTGACAGGCAAAGAAAGAGAACTCAGTGTAGGTAGAATGTTTGCAATGCAACCG
GGAATGTTCAGACAGGTTCAAATATTGGCAGAGAAAATGATAGCTGAAAACATTTT
ACAATTCTTTCCTGAAAGTCTTACAAGATATGGTGATCTAGAACTACAAAAAATATT
AGAATTGAAAGCAGGAATAAGTAACAAATCAAATCGCTACAATGATAATTACAACA
ATTACATTAGTAAGTGCTCTATCATCACAGATCTCAGCAAATTCAATCAAGCATTTC
```

```
-continued
GATATGAAACGTCATGTATTTGTAGTGATGTGCTGGATGAACTGCATGGTGTACAAT

CTCTATTTTCCTGGTTACATTTAACTATTCCTCATGTCACAATAATATGCACATATAG

GCATGCACCCCCCTATATAGGAGATCATATTGTAGATCTTAACAATGTAGATGAACA

AAGTGGATTATATAGATATCACATGGGTGGCATCGAAGGGTGGTGTCAAAAACTGT

GGACCATAGAAGCTATATCACTATTGGATCTAATATCTCTCAAAGGGAAATTCTCAA

TTACTGCTTTAATTAATGGTGACAATCAATCAATAGATATAAGCAAACCAATCAGAC

TCATGGAAGGTCAAACTCATGCTCAAGCAGATTATTTGCTAGCATTAAATAGCCTTA

AATTACTGTATAAAGAGTATGCAGGCATAGGCCACAAATTAAAAGGAACTGAGACT

TATATATCACGAGATATGCAATTTATGAGTAAAACAATTCAACATAACGGTGTATAT

TACCCAGCTAGTATAAAGAAAGTCCTAAGAGTGGGACCGTGGATAAACACTATACT

TGATGATTTCAAAGTGAGTCTAGAATCTATAGGTAGTTTGACACAAGAATTAGAATA

TAGAGGTGAAAGTCTATTATGCAGTTTAATATTTAGAAATGTATGGTTATATAATCA

GATTGCTCTACAATTAAAAAATCATGCATTATGTAACAATAAACTATATTTGGACAT

ATTAAAGGTTCTGAAACACTTAAAAACCTTTTTTAATCTTGATAATATTGATACAGC

ATTAACATTGTATATGAATTTACCCATGTTATTTGGTGGTGGTGATCCCAACTTGTTA

TATCGAAGTTTCTATAGAAGAACTCCTGACTTCCTCACAGAGGCTATAGTTCACTCT

GTGTTCATACTTAGTTATTATACAAACCATGACTTAAAAGATAAACTTCAAGATCTG

TCAGATGATAGATTGAATAAGTTCTTAACATGCATAATCACGTTTGACAAAAACCCT

AATGCTGAATTCGTAACATTGATGAGAGATCCTCAAGCTTTAGGGTCTGAGAGACAA

GCTAAAATTACTAGCGAAATCAATAGACTGGCAGTTACAGAGGTTTTGAGTACAGCT

CCAAACAAAATATTCTCCAAAAGTGCACAACATTATACTACTACAGAGATAGATCTA

AATGATATTATGCAAAATATAGAACCTACATATCCTCATGGGCTAAGAGTTGTTTAT

GAAAGTTTACCCTTTTATAAAGCAGAGAAAATAGTAAATCTTATATCAGGTACAAAA

TCTATAACTAACATACTGGAAAAAACTTCTGCCATAGACTTAACAGATATTGATAGA

GCCACTGAGATGATGAGGAAAAACATAACTTTGCTTATAAGGATACTTCCATTGGAT

TGTAACAGAGATAAAAGAGAGATATTGAGTATGGAAAACCTAAGTATTACTGAATT

AAGCAAATATGTTAGGGAAAGATCTTGGTCTTTATCCAATATAGTTGGTGTTACATC

ACCCAGTATCATGTATACAATGGACATCAAATATACTACAAGCACTATATCTAGTGG

CATAATTATAGAGAAATATAATGTTAACAGTTTAACACGTGGTGAGAGAGGACCCA

CTAAACCATGGGTTGGTTCATCTACACAAGAGAAAAAAACAATGCCAGTTTATAAT

AGACAAGTCTTAACCAAAAAACAGAGAGATCAAATAGATCTATTAGCAAAATTGGA

TTGGGTGTATGCATCTATAGATAACAAGGATGAATTCATGGAAGAACTCAGCATAG

GAACCCTTGGGTTAACATATGAAAAGGCCAAGAAATTATTTCCACAATATTTAAGTG

TCAATTATTTGCATCGCCTTACAGTCAGTAGTAGACCATGTGAATTCCCTGCATCAAT

ACCAGCTTATAGAACAACAAATTATCACTTTGACACTAGCCCTATTAATCGCATATT

AACAGAAAAGTATGGTGATGAAGATATTGACATAGTATTCCAAAACTGTATAAGCT

TTGGCCTTAGTTTAATGTCAGTAGTAGAACAATTTACTAATGTATGTCCTAACAGAA

TTATTCTCATACCTAAGCTTAATGAGATACATTTGATGAAACCTCCCATATTCACAG

GTGATGTTGATATTCACAAGTTAAAACAAGTGATACAAAAACAGCATATGTTTTTAC

CAGACAAAATAAGTTTGACTCAATATGTGGAATTATTCTTAAGTAATAAAACACTCA

AATCTGGATCTCATGTTAATTCTAATTTAATATTGGCACATAAAATATCTGACTATTT
```

-continued

```
TCATAATACTTACATTTTAAGTACTAATTTAGCTGGACATTGGATTCTGATTATACAA

CTTATGAAAGATTCTAAAGGTATTTTTGAAAAAGATTGGGGAGAGGGATATATAACT

GATCATATGTTTATTAATTTGAAAGTTTTCTTCAATGCTTATAAGACCTATCTCTTGT

GTTTTCATAAAGGTTATGGCAAAGCAAAGCTGGAGTGTGATATGAACACTTCAGATC

TTCTATGTGTATTGGAATTAATAGACAGTAGTTATTGGAAGTCTATGTCTAAGGTATT

TTTAGAACAAAAAGTTATCAAATACATTCTTAGCCAAGATGCAAGTTTACATAGAGT

AAAAGGATGTCATAGCTTCAAATTATGGTTTCTTAAACGTCTTAATGTAGCAGAATT

CACAGTTTGCCCTTGGGTTGTTAACATAGATTATCATCCAACACATATGAAAGCAAT

ATTAACTTATATAGATCTTGTTAGAATGGGATTGATAAATATAGATAGAATACACAT

TAAAAATAAACACAAATTCAATGATGAATTTTATACTTCTAATCTCTTCTACATTAAT

TATAACTTCTCAGATAATACTCATCTATTAACTAAACATATAAGGATTGCTAATTCTG

AATTAGAAAATAATTACAACAAATTATATCATCCTACACCAGAAACCCTAGAGAAT

ATACTAGCCAATCCGATTAAAAGTAATGACAAAAAGACACTGAATGACTATTGTAT

AGGTAAAAATGTTGACTCAATAATGTTACCATTGTTATCTAATAAGAAGCTTATTAA

ATCGTCTGCAATGATTAGAACCAATTACAGCAAACAAGATTTGTATAATTTATTCCC

TATGGTTGTGATTGATAGAATTATAGATCATTCAGGCAATACAGCCAAATCCAACCA

ACTTTACACTACTACTTCCCACCAAATATCTTTAGTGCACAATAGCACATCACTTTAC

TGCATGCTTCCTTGGCATCATATTAATAGATTCAATTTTGTATTTAGTTCTACAGGTT

GTAAAATTAGTATAGAGTATATTTAAAAGATCTTAAAATTAAAGATCCCAATTGTA

TAGCATTCATAGGTGAAGGAGCAGGGAATTTATTATTGCGTACAGTAGTGGAACTTC

ATCCTGACATAAGATATATTTACAGAAGTCTGAAAGATTGCAATGATCATAGTTTAC

CTATTGAGTTTTTAAGGCTGTACAATGGACATATCAACATTGATTATGGTGAAAATT

TGACCATTCCTGCTACAGATGCAACCAACAACATTCATTGGTCTTATTTACATATAA

AGTTTGCTGAACCTATCAGTCTTTTTGTCTGTGATGCCGAATTGTCTGTAACAGTCAA

CTGGAGTAAAATTATAATAGAATGGAGCAAGCATGTAAGAAAGTGCAAGTACTGTT

CCTCAGTTAATAAATGTATGTTAATAGTAAAATATCATGCTCAAGATGATATTGATT

TCAAATTAGACAATATAACTATATTAAAAACTTATGTATGCTTAGGCAGTAAGTTAA

AGGGATCGGAGGTTTACTTAGTCCTTACAATAGGTCCTGCGAATATATTCCCAGTAT

TTAATGTAGTACAAAATGCTAAATTGATACTATCAAGAACCAAAAATTTCATCATGC

CTAAGAAAGCTGATAAAGAGTCTATTGATGCAAATATTAAAAGTTTGATACCCTTTC

TTTGTTACCCTATAACAAAAAAGGAATTAATACTGCATTGTCAAAACTAAAGAGTG

TTGTTAGTGGAGATATACTATCATATTCTATAGCTGGACGTAATGAAGTTTTCAGCA

ATAAACTTATAAATCATAAGCATATGAACATCTTAAAATGGTTCAATCATGTTTTAA

ATTTCAGATCAACAGAACTAAACTATAACCATTTATATATGGTAGAATCTACATATC

CTTACCTAAGTGAATTGTTAAACAGCTTGACAACCAATGAACTTAAAAAACTGATTA

AAATCACAGGTAGTCTGTTATACAACTTTCATAATGAATAATGAATAAAGATCTTAT

AATAAAAATTCCCATAGCTATACACTAACACTGTATTCAATTATAGTTATTAAAAAT

TAAAAATCGTACGATTTTTTAAATAACTTTTAGTGAACTAATCCTAAAGTTATCATTT

TAATCTTGGAGGAATAAATTTAAACCCTAATCTAATTGGTTTATATGTGTATTAACTA

AATTACGAGATATTAGTTTTTGACACTTTTTTTCTCGT
``` or variants having greater than 50, 60, 70, 80, 90, 95, 98, or 99% sequence identity.

In certain embodiments, the chimeric RSV includes those which are infectious to a human subject and those which are not infectious to a human subject.

In certain embodiments, the disclosure relates to a particle, RSV particle, or virus like particle comprising a mutated RSV F protein disclosed herein. In certain embodiments, the particle comprises a live and infectious attenuated RSV genome or antigenome. In certain embodiments, the particle comprises and inactivated RSV genome or antigenome, e.g., without nucleic acids or with nucleic acids that are not capable of expressing one, two, three or more or any of the RSV proteins. In certain embodiments, the particles are killed using a method such as heat or formaldehyde. In certain embodiments, the particles are reconstituted by expression of viral structural proteins and the mutated RSV F proteins disclosed herein.

BRIEF DESCRIPTION OF THE FIGURES

FIG. 1 illustrates an RSV sequence comparison of an F protein having a 1557 V mutation (Query) (SEQ ID NO: 3) and the typical wild type RSV strain line 19 sequence (Sbjct) (SEQ ID NO: 4).

FIG. 5A illustrates the sequence of an F protein with substitution of M at position 79, R at position 191, K at position 357, and Y at position 371 designated as DB1 QUAD (Query) (SEQ ID NO: 1) when compared to a consensus sequence (Sbjct) (SEQ ID NO: 2) for a low-fusion RSV subgroup B strain of the Buenos Aires clade (BAF).

FIG. 5B illustrates a comparison of the amino acid sequences of the DB1 QUAD F protein (Query) (SEQ ID NO: 1) and the typical wild type RSV strain line 19 sequence (Sbjct) (SEQ ID NO: 4). There is an identity of 519/573 (91%) and similarity of 548/573 (95%).

DETAILED DESCRIPTION

Figure 2:
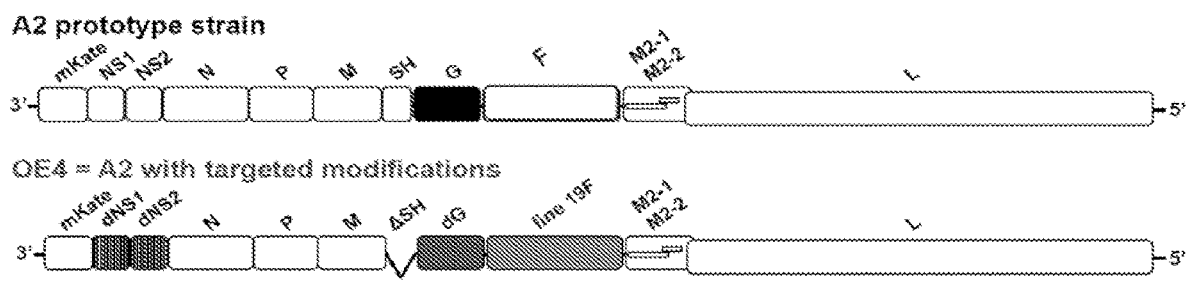
FIG. 2 illustrates the RSV vaccine candidate OE4. RSV with codon-deoptimized NS1 and NS2 (dNS1/dNS2) is genetically stable and attenuates RSV while retaining immunogenicity like wild type virus A2. OE4 also has codon-deoptimization of the G protein, deletion of the SH protein, and expresses RSV line 19 F protein.
Figure 3:
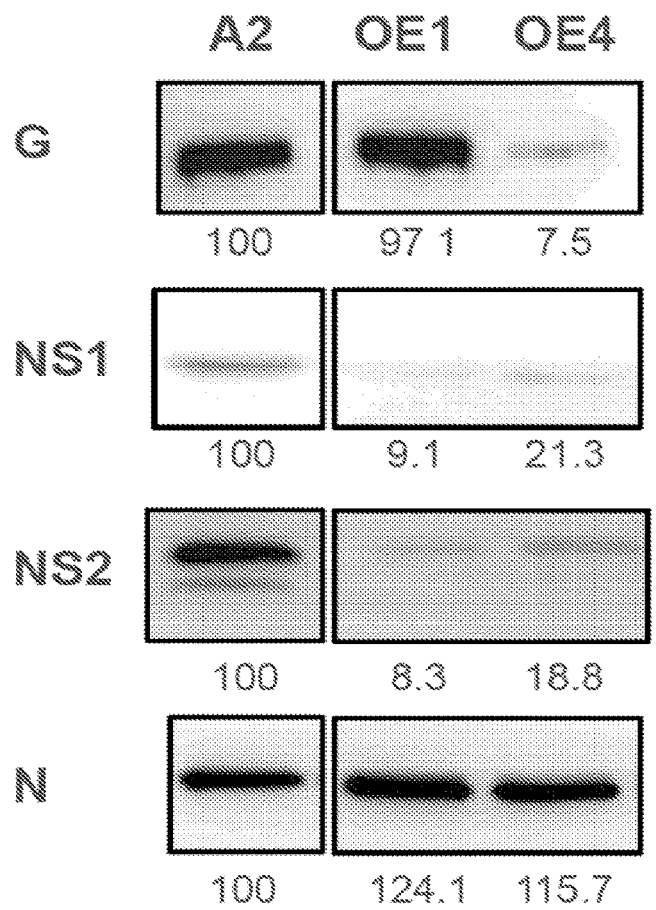
FIG. 3 shows westerns of Vero cell lysates indicating reduced protein expression for the codon-deoptimized RSV G, NS1, NS2 genes when the RSVs infect Vero cells.
Figure 4:
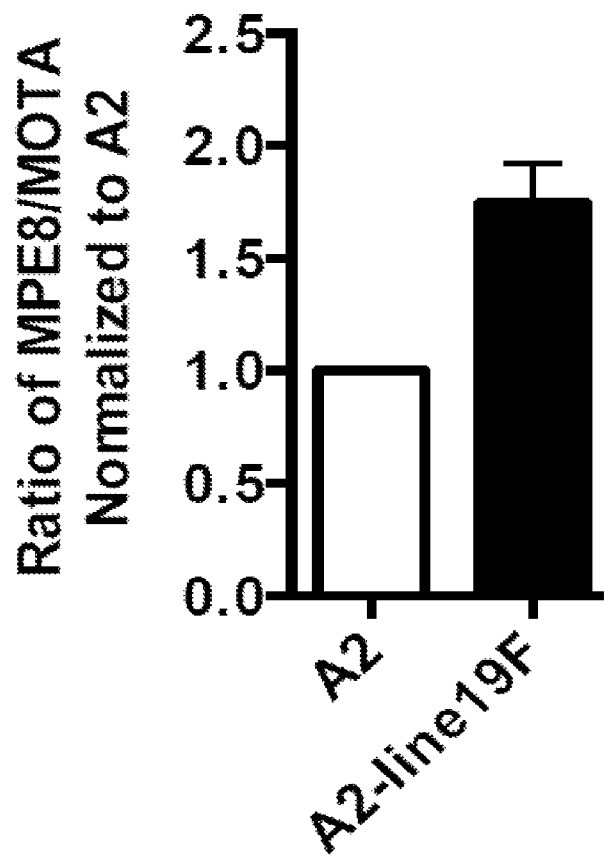
FIG. 4 shows data indicating chimeric, RSV, expressing, Line 19 F (A2 Line 19F) exhibits a pre-fusion F bias compared to RSV F of strain A2.
Figure 6A:
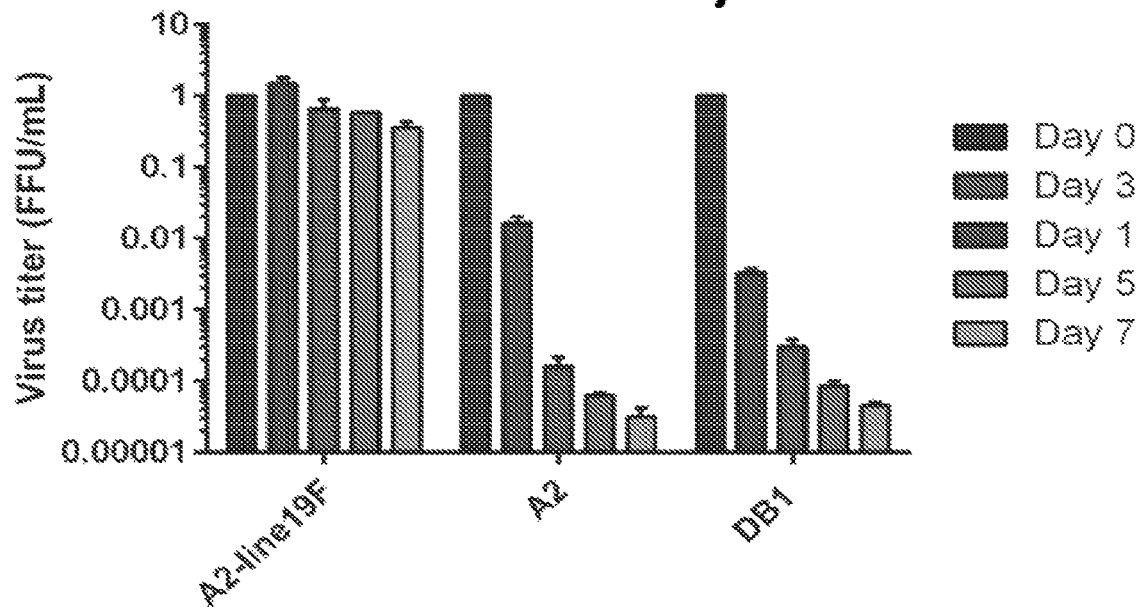
FIG. 6A shows data on the thermostability of certain RSV constructs after 7 days including DB1 which contains the consensus F protein of SEQ ID NO: 2.
Figure 6B:
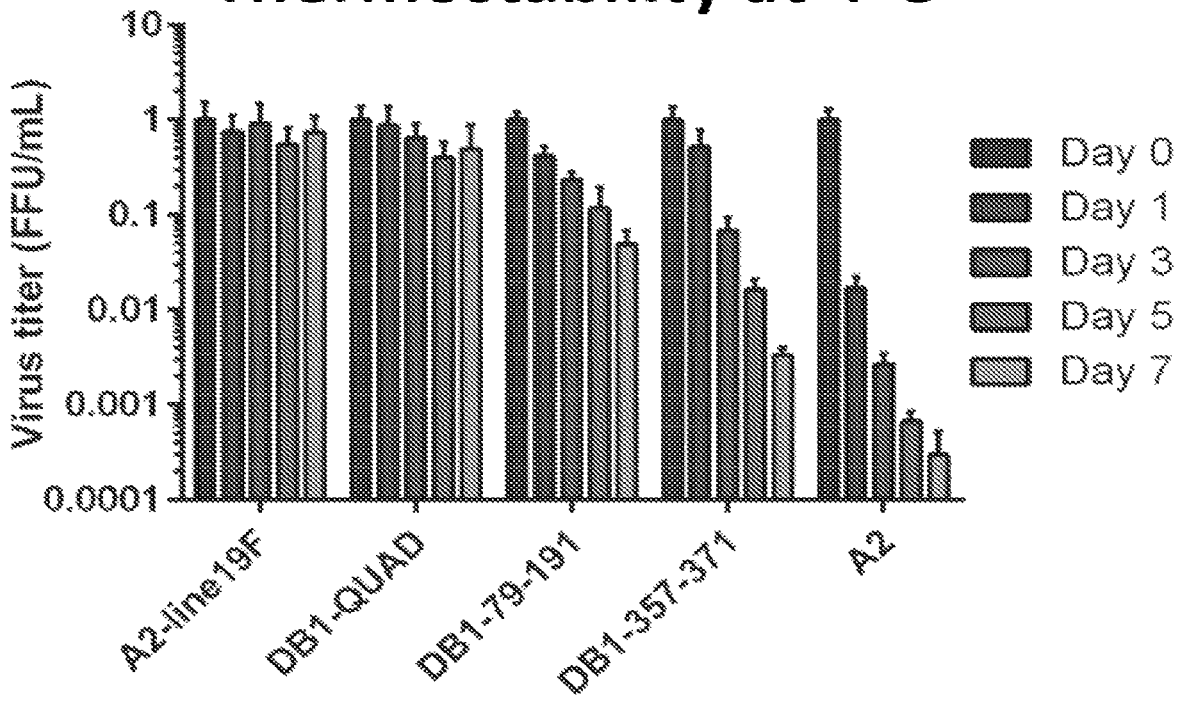
FIG. 6B shows data on thermostability of certain RSV constructs after 7 days including a DB1 construct containing F protein amino acids that correspond to certain positions found in the F protein of line19. The DB1 QUAD refers to the F protein having SEQ ID NO: 1 including an amino acid pattern of M at position 79, R at position 191, K at position 357, and Y at position 371, and V at position 557.
Figure 6C:
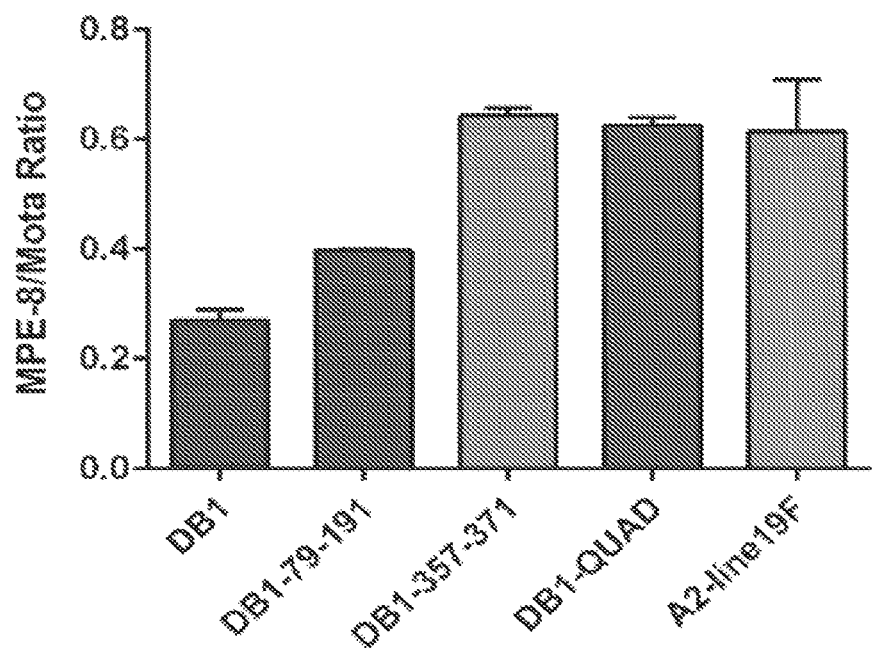
FIG. 6C shows data indicating the ratio of pre-fusion F to total F (pre-fusion and post-fusion F) of certain vaccine candidates.
Figure 7A:
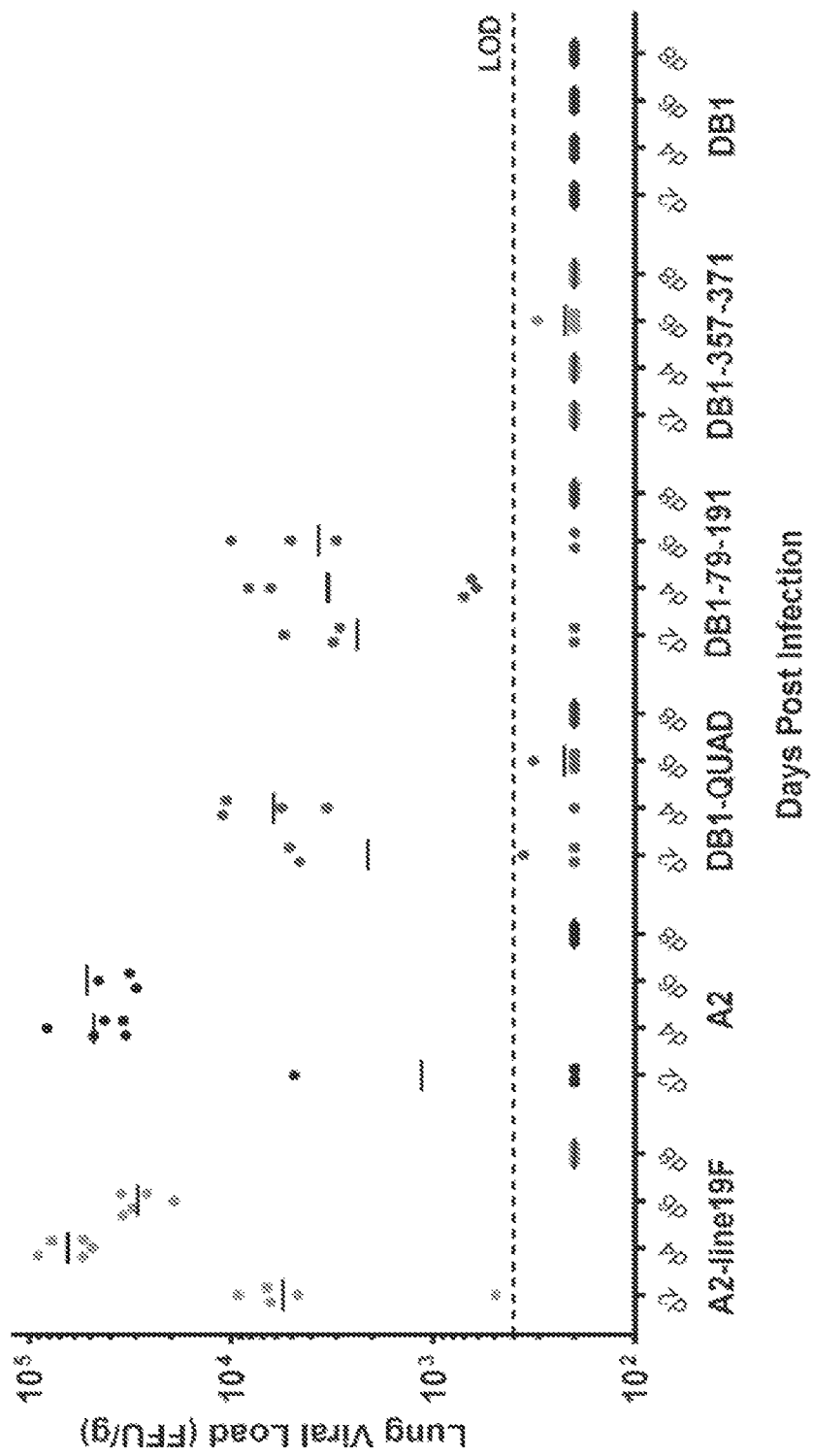
FIG. 7A shows data on the attenuation of vaccine constructs in BALB/c mice indicating that DB1 QUAD was more attenuated when compared to the A2-Line19F.
Figure 7B:
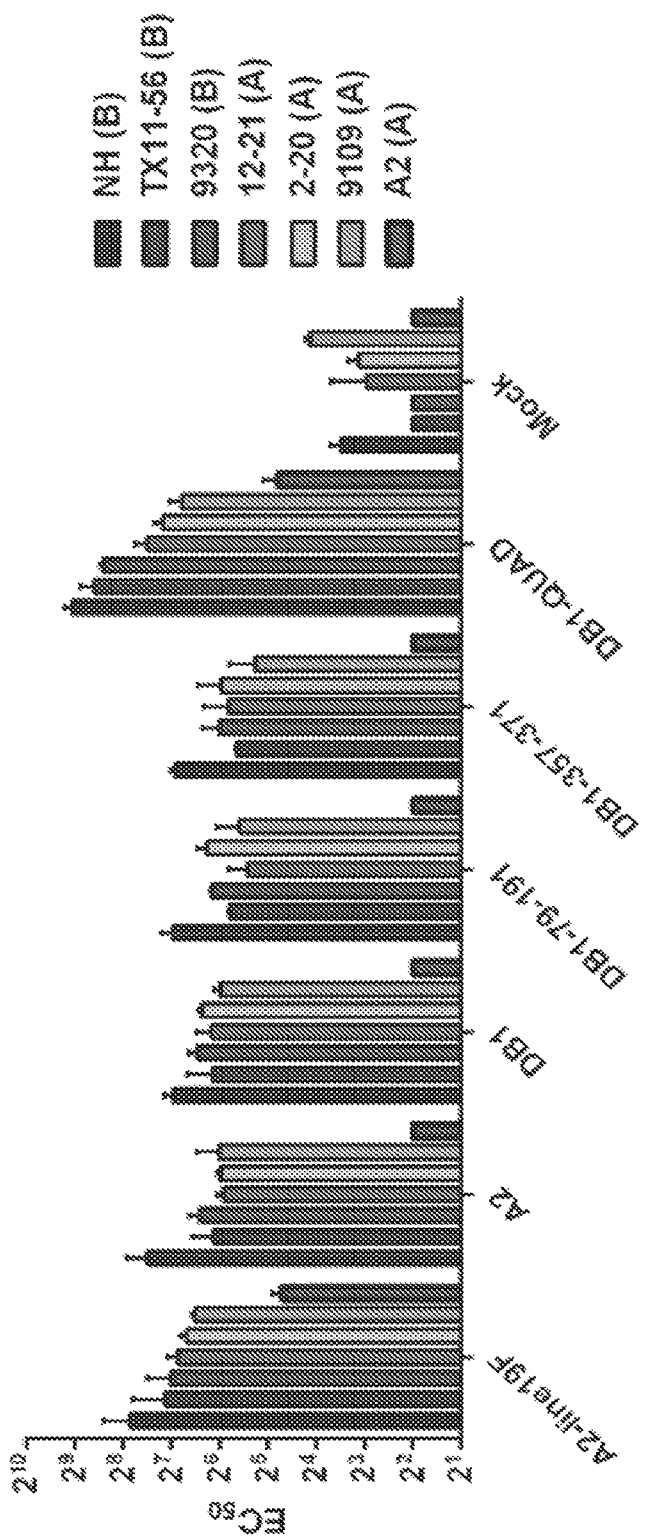
FIG. 7B shows data on the immunogenicity of vaccine constructs in BALB/c mice against different RSV strains indicating DB1 QUAD increased immunogenicity against RSV B.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

The terms "protein" and "polypeptide" refer to compounds comprising amino acids joined via peptide bonds and are used interchangeably.

The term "portion" when used in reference to a protein (as in "a portion of a given protein") refers to fragments of that protein. The fragments may range in size from four amino acid residues to the entire amino sequence minus one amino acid.

The terms "chimeric respiratory syncytial virus" or "chimeric RSV" refer to a nucleic acid that contains sufficient RSV genes to allow the genome or antigenome to replicate in host cells (e.g. Vero cells) and the sequence nucleic acid is altered to include at least one nucleic acid segment that is not structurally the same a natural RSV strain, i.e., as the RSV strain occurs naturally over the whole RSV genome. A chimeric respiratory syncytial virus includes an RSV gene wherein the codons are altered to be different from those naturally occurring even though the RSV produces a polypeptide with an identical amino acid sequence to those naturally expressed. Different strains of RSV will have different nucleotide sequences and express proteins with different amino acid sequences that have similar functions. Thus, a chimeric RSV includes an RSV gene wherein one or more genes from one strain are replaced from genes in alternative or second strain such that the nucleic acid sequence of the entire RSV genome is not identical to an RSV found in nature. In certain embodiments, the chimeric RSV includes those strains where nucleic acids are deleted after a codon for starting translation in order to truncate the proteins expression, provided such truncation pattern for the genome is not found in naturally occurring RSV. In certain embodiments, the chimeric RSV includes those which are infectious and can replicate in a human subject.

The term "fusion" when used in reference to a polypeptide refers to the expression product of two or more coding sequences obtained from different sources such that they do not exist together in a natural environment, that have been cloned together and that, after translation, act as a single polypeptide sequence. Fusion polypeptides are also referred to as "hybrid" polypeptides. The coding sequences include those obtained from the same or from different species of organisms.

However, this type of fusion protein is not the same as the RSV fusion protein in the disclosed vaccines. The RSV fusion protein (F) is a major surface glycoprotein that causes the virion membrane to fuse to the target cell membrane. The fusion protein exists in a metastable pre-fusion conformation that subsequently undergoes major refolding into a stable post-fusion form that approximates virion and target cell membranes and enables fusion. The F protein is highly conserved among RSV strains and is a potent RSV immunogen. After natural infection in humans, the majority of anti-RSV neutralizing antibodies are directed against the F protein, specifically against the pre-fusion conformation of F.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a polynucleotide having a nucleotide sequence encoding a gene" or "a polynucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2:482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic-F Y W; hydrophobic-A V I L; Charged positive: R K H; Charged negative-D E; Polar-S T N Q.

The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present disclosure.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and are found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, a "regulatable" or "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

Efficient expression of recombinant DNA sequences in eukaryotic cells typically requires expression of signals directing the efficient termination and polyadenylation of the resulting transcript. Transcription termination signals are generally found downstream of the polyadenylation signal and are a few hundred nucleotides in length. The term "poly (A) site" or "poly (A) sequence" as used herein denotes a DNA sequence which directs both the termination and polyadenylation of the nascent RNA transcript. Efficient polyadenylation of the recombinant transcript is desirable, as transcripts lacking a poly (A) tail are unstable and are rapidly degraded. The poly (A) signal utilized in an expression vector may be "heterologous" or "endogenous." An endogenous poly (A) signal is found naturally at the 3' end of the coding region of a given gene in the genome. A heterologous poly (A) signal is one which has been isolated from one gene and positioned 3' to another gene. A commonly used heterologous poly (A) signal is the SV40 poly (A) signal. The SV40 poly (A) signal is contained on a 237 bp BamHI/BclI restriction fragment and directs both termination and polyadenylation.

The term "vector" refers to nucleic acid molecules that transfer DNA segment(s) from one cell to another. The term "vehicle" is sometimes used interchangeably with "vector."

The terms "expression vector" or "expression cassette" refer to a recombinant nucleic acid containing a desired coding sequence and appropriate nucleic acid sequences used for the expression of the operably linked coding sequence in a particular host organism. Nucleic acid sequences used for expression in prokaryotes typically include a promoter, an operator (optional), and a ribosome binding site, often along with other sequences. Eukaryotic cells are known to utilize promoters, enhancers, and termination and polyadenylation signals.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-B-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose: galactose-1-phosphate uridyltransferasel (galT), feedback-insensitive a subunit of anthranilate synthase (OASAID), 2-deoxyglucose (2-DOGR), benzyladenine-N-3-glucuronide, F. *coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as 35S or 131I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to the recombinant vectors comprising a nucleic acid encoding a polypeptide disclosed herein or fusion protein thereof.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

The term "reporter gene" refers to a gene encoding a protein that may be assayed. Examples of reporter genes include, but are not limited to, modified katushka, mkate and mkate2 (See, e.g., Merzlyak et al., Nat. Methods, 2007, 4, 555-557 and Shcherbo et al., Biochem. J., 2008, 418, 567-574), luciferase (See, e.g., deWet et al., Mol. Cell. Biol. 7:725 (1987) and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from ClonTech Laboratories, Palo Alto, Calif.), chloramphenicol acetyltransferase, beta-galactosidase, alkaline phosphatase, and horse radish peroxidase.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" or "antigenome" refers to a nucleotide sequence whose sequence of nucleotide residues is in reverse 5' to 3' orientation in relation to the sequence of nucleotide residues in a sense strand. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex.

The term "isolated" refers to a biological material, such as a virus, a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

An "immunologically effective amount" of RSV is an amount sufficient to enhance an individual's (e.g., a human's) own immune response against a subsequent exposure to RSV. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against RSV refers to an immune response exhibited by an individual (e.g., a human) that is protective against serious lower respiratory tract disease (e.g., pneumonia and/or bronchiolitis) when the individual is subsequently exposed to and/or infected with wild-type RSV.

Chimeric Respiratory Syncytial Virus (RSV)

Naturally occurring RSV particles typically contain a viral genome within a helical nucleocapsid which is surrounded by matrix proteins and an envelope containing glycoproteins. The genome of human wild-type RSVs encode the proteins, NS1, NS2, N, P, M, SH, G, F, M2-1, M2-2, and L. G, F, and SH are glycoproteins. RSV polymerase activity consists of the large protein (L.) and phosphoprotein (P). The viral M2-1 protein is used during transcription and is likely to be a component of the transcriptase complex. The viral N protein is used to encapsidate the nascent RNA during replication.

The genome is transcribed and replicated in the cytoplasm of a host cell. Host-cell transcription typically results in synthesis of ten methylated and polyadenylated mRNAs. The antigenome is positive-sense RNA complement of the genome produced during replication, which in turn acts as a template for genome synthesis. The viral genes are flanked by conserved gene-start (GS) and gene-end (GE) sequences. At the 3' and 5' ends of the genome are leader and trailer nucleotides. The wild type leader sequence contains a promoter at the 3' end. When the viral polymerase reaches a GE signal, the polymerase polyadenylates and releases the mRNA and reinitiates RNA synthesis at the next GS signal. The L-P complex is believed to be responsible for recognition of the promoter, RNA synthesis, capping and methylation of the 5' termini of the mRNAs and polyadenylation of their 3' ends. It is believed that the polymerase sometimes dissociates from the gene at the junctions. Because the polymerase initiates transcription at the 3' end of the genome, this results in a gradient of expression, with the genes at the 3' end of the genome being transcribed more frequently than those at the 5' end.

To replicate the genome, the polymerase does not respond to the cis-acting GE and GS signals and generates positive-sense RNA complement of the genome, the antigenome. At the 3' end of the antigenome is the complement of the trailer, which contains a promoter. The polymerase uses this promoter to generate genome-sense RNA. Unlike mRNA, which is released as naked RNA, the antigenome and genome RNAs are encapsidated with virus nucleoprotein (N) as they are synthesized.

After translation of viral mRNAs, a full-length (+) antigenomic RNA is produced as a template for replication of the (−) RNA genome. Infectious recombinant RSV (rRSV) particles may be recovered from transfected plasmids. Co-expression of RSV N, P, L, and M2-1 proteins as well as the full-length antigenomic RNA is sufficient for RSV replication. See Collins et al., Proc Natl Acad Sci USA., 1995, 92 (25): 11563-11567 and U.S. Pat. No. 6,790,449.

In certain embodiments, the disclosure relates to certain desirable sequence of RSV F polypeptides and recombinant nucleic acids encoding the same. In certain embodiments, the disclosure contemplates recombinant vectors comprising nucleic acids encoding these polypeptides and cells comprising said vectors. In certain embodiments, the vector comprises a selectable marker or reporter gene.

Common vectors for storing RSV include plasmids and bacterial artificial chromosomes (BAC). Typically, a bacterial artificial chromosome comprises one or more genes selected from the group consisting of oriS, repE, parA, and parB genes of Factor F in operable combination with a selectable marker, e.g., a gene that provides resistance to an antibiotic. The nucleic acid sequence may be the genomic or antigenomic sequence of the virus which is optionally mutated, e.g., RSV strain which is optionally mutated.

Cultivating RSV in *E. coli* bacteria may be accomplished by utilizing a bacterial artificial chromosome (BAC). A BAC vector for storing and genetically engineering RSV is reported in Stobart et al., Methods Mol Biol., 2016, 1442: 141-53 and U.S. Patent Application Publication number 2012/0264217. The disclosed BAC contains the complete antigenomic sequence of respiratory syncytial virus (RSV) strain A2 except the F gene, which is the antigenomic sequence of RSV strain line 19. Along with helper plasmids, it can be used in the reverse genetics system for the recovery of infectious virus. The antigenome sequence on the plasmid can be mutated prior to virus recovery to generate viruses with desired mutations.

In certain embodiments, the disclosure relates to methods of generating respiratory syncytial virus (RSV) particles comprising inserting a vector with a BAC gene and a RSV antigenome into an isolated eukaryotic cell and inserting one or more vectors selected from the group consisting of: a vector encoding an N protein of RSV, a vector encoding a P protein of RSV, a vector encoding an L protein of RSV, and a vector encoding an M2-1 protein of RSV into the cell under conditions such that RSV virion is formed. Inserting a vector into a cell may occur by physically injecting, electroporating, or mixing the cell and the vector under conditions such that the vector enters the cell.

Chimeric RSV is contemplated to include certain mutations, deletions, or variant combinations, such as cold-passaged (cp) non-temperature sensitive (ts) derivatives of RSV, cpRSV, such as rA2cp248/404/1030ΔSH. rA2cp248/404ΔSH contains 4 independent attenuating genetic elements: cp which is based on 5 missense mutations in the N and L proteins and the F glycoprotein that together confer the non-ts attenuation phenotype of cpRSV; ts248, a missense mutation in the L protein; ts404, a nucleotide substitution in the gene-start transcription signal of the M2 gene; and ΔSH, complete deletion of the SH gene. rA2cp248/404/1030ΔSH contains 5 independent attenuating genetic elements: those present in rA2cp248/404ΔSH and ts1030, another missense mutation in the L protein. See Karron et al., J Infect Dis., 2005, 191 (7): 1093-1104, hereby incorporated by reference. Within certain embodiments, it is contemplated that the RSV anitgenome may contain deletion or mutations in nonessential genes (e.g., the SH, NS1, NS2, and M2-2 genes) or combinations thereof.

Due to the redundancy of the genetic code, individual amino acids are encoded by multiple sequences of codons, sometimes referred to as synonymous codons. In different species, synonymous codons are used more or less frequently, sometimes referred to as codon bias. Genetic engineering of under-represented synonymous codons into the coding sequence of a gene has been shown to result in decreased rates of protein translation without a change in the amino acid sequence of the protein. Mueller et al. report virus attenuation by changes in codon bias. See, Science, 2008, 320:1784. See also WO/2008121992, WO/2006042156, Burns et al., J Virology, 2006, 80 (7): 3259 and Mueller et al., J Virology, 2006, 80 (19): 9687.

Usage of codon deoptimization in RSV is reported in Meng, et al., MBio 5, e01704-01714 (2014) and U.S. Patent Application Publication number 2016/0030549. In certain embodiments, this disclosure relates to isolated nucleic acids, recombinant respiratory syncytial virus (RSV) with codon deoptimization, vaccines produced therefrom, and vaccination methods related thereto. In certain embodiments, the codon deoptimization is in the nonstructural genes NS1 and NS2 and optionally in a gene G and optionally in a gene L. In further embodiments, the gene SH is deleted. In further embodiments, the gene F is mutated, e.g., RSV F protein having an amino acid pattern of M at position 79, R at position 191, K at position 357, and Y at position 371, and a V at position 557.

In certain embodiments, the disclosure relates to isolated nucleic acids encoding deoptimized genes NS1 and/or NS2 and optionally the gene G and optionally the gene I, of a wild-type human RSV or variant wherein the nucleotides are substituted such that a codon to produce Gly is GGT, a codon to produce Asp is GAT, a codon to produce Glu is GAA, a codon to produce His is CAT, a codon to produce Ile is ATA, a codon to produce Lys is AAA, a codon to produce Leu is CTA, a codon to produce Asn is AAT, a codon to produce Gln is CAA, a codon to produce Val is GTA, or a codon to produce Tyr is TAT, or combinations thereof. In certain embodiments, a gene in the isolated nucleic acid further comprises a combination of at least two, three, four, five, six, seven, eight nine, ten, or all of the individual codons. In certain embodiment, a gene in the isolated nucleic acid comprises at least 20, 30, 40, or 50 or more of the codons.

In certain embodiments, this disclosure relates to isolated nucleic acid as disclosed herein wherein the nucleotides are substituted such that a codon to produce Ala is GCG, a codon to produce Cys is TGT, a codon to produce Phe is TTT, a codon to produce Pro is CCG, a codon to produce Arg is CGT, a codon to produce Ser is TCG, or a codon to produce Thr is ACG, or combinations thereof. In certain embodiments, a gene containing the nucleic acid comprises a combination of at least two, three, four, five, six, seven, eight nine, ten, eleven, twelve, thirteen, fourteen, fifteen, sixteen, or all of the individual codons. In certain embodiments, a gene in the isolated nucleic acid further comprises at least 20, 30, 40, or 50 or more of the codons.

Glenn et al. report a randomized, blinded, controlled, dose-ranging study of a respiratory syncytial virus recombinant fusion (F) nanoparticle vaccine in healthy women of childbearing age. J Infect Dis. 2016, 213 (3): 411-22. In certain embodiments, this disclosure relates to virus particles and virus-like particles (VLPs) that contain a mutated F protein reported herein. Virus particles are commonly used as an inactivated vaccine (or killed vaccine). RSV can be grown in culture and then killed using a method such as heat or formaldehyde. Live attenuated vaccines are typically weakened such that rate of replication and/or infection is slower.

In certain embodiments, the disclosure contemplates a chimeric RSV particle as a whole virus vaccine, e.g., the entire virus particle exposed to heat, chemicals, or radiation such that the genome of the RSV is non-replicative or non-infectious. In certain embodiments, the disclosure contemplates a chimeric RSV particle in a split virus vaccine produced by using a detergent to disrupt the virus and by purifying out the mutated F proteins disclosed herein as antigens to stimulate the immune system to mount a response to the virus.

VLPs closely resemble mature virions, but they do not contain viral genomic material (i.e., viral genomic RNA). Therefore, VLPs are non-replicative in nature. In addition, VLPs can express proteins on the surface of the VLP. Moreover, since VLPs resemble intact virions and are multivalent particulate structures, VLPs can be effective in inducing neutralizing antibodies to the surface protein. VLPs can be administered repeatedly.

In certain embodiments, the disclosure contemplates VLP comprising a mutated F protein disclosed herein on the surface and an influenza virus matrix (M1) protein core. Quan et al. report methods of producing virus-like particles (VLPs) made-up of an influenza virus matrix (M1) protein core and RSV-F on the surface J Infect Dis. 2011, 204 (7): 987-995. One can generate recombinant baculoviruses (rBVs) expressing RSV F and influenza M1 and transfect them into insect cells for production.

Methods of Use

In certain embodiments, the disclosure relates to immunogenic compositions comprising an immunologically effective amount of a chimeric respiratory syncytial virus (RSV), RSV polypeptide, RSV particle, RSV virus-like particle, and/or nucleic acid disclosed herein. In certain embodiments, the disclosure relates to methods for stimulating the immune system of an individual to produce a protective immune response against RSV. In certain embodiments, an immunologically effective amount of a chimeric RSV, polypeptide, and/or nucleic acid disclosed herein is administered to the individual in a physiologically acceptable carrier.

In certain embodiments, the disclosure relates to medicaments and vaccine products comprising nucleic acids disclosed herein for uses disclosed herein.

In certain embodiments, the disclosure relates to the use of nucleic acids or vectors disclosed herein for the manufacture of a medicament for uses disclosed herein.

The disclosure also provides the ability to analyze other types of attenuating mutations and to incorporate them into chimeric RSV for vaccine or other uses. For example, a tissue culture-adapted nonpathogenic strain of pneumonia virus of mice (the murine counterpart of RSV) lacks a cytoplasmic tail of the G protein (Randhawa et al., Virology 207:240-245 (1995)). By analogy, the cytoplasmic and transmembrane domains of each of the RSV glycoproteins, F, G and SH, can be deleted or modified to achieve attenuation.

Other mutations for use in infectious RSV of the present disclosure include mutations in cis-acting signals identified during mutational analysis of RSV minigenomes. For example, insertional and deletional analysis of the leader and trailer and flanking sequences identified viral promoters and transcription signals and provided a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into the complete antigenome or genome as described herein. Other mutations involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986), incorporated herein by reference) can be shortened or lengthened or changed in sequence content, and the naturally-occurring gene overlap (Collins et al., Proc. Natl. Acad. Sci. USA 84:5134-5138 (1987), incorporated herein by reference) can be removed or changed to a different intergenic region by the methods described herein.

For vaccine use, virus produced according to the present disclosure can be used directly in vaccine formulations, or lyophilized, as desired, using lyophilization protocols well known to the artisan. Lyophilized virus will typically be maintained at about 4 degrees C. When ready for use the lyophilized virus is reconstituted in a stabilizing solution, e.g., saline or comprising SPG, Mg, and HEPES, with or without adjuvant, as further described below.

Typically, the RSV vaccines of the disclosure contain as an active ingredient an immunogenetically effective amount of RSV produced as described herein. The modified virus may be introduced into a subject with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art.

Upon immunization with a RSV composition as described herein, via aerosol, droplet, oral, topical or other route, the immune system of the subject responds to the vaccine by producing antibodies specific for RSV virus proteins, e.g., F glycoproteins. As a result of the vaccination the subject becomes at least partially or completely immune to RSV infection, or resistant to developing moderate or severe RSV infection, particularly of the lower respiratory tract.

The subject to which the vaccines are administered can be any mammal which is susceptible to infection by RSV or a closely related virus and which subject is capable of generating a protective immune response to the antigens of the vaccinating strain. Thus, suitable subjects include humans, non-human primates, bovine, equine, swine, ovine, caprine, lagamorph, rodents, etc. Accordingly, the disclosure provides methods for creating vaccines for a variety of human and veterinary uses.

The vaccine compositions containing the RSV of the disclosure are administered to a subject susceptible to or otherwise at risk of RSV infection to enhance the subject's own immune response capabilities. Such an amount is defined to be an "immunogenically effective dose." In this use, the precise amounts again depend on the subject's state of health and weight, the mode of administration, the nature of the formulation. The vaccine formulations should provide a quantity of modified RSV of the disclosure sufficient to effectively protect the subject patient against serious or life-threatening RSV infection.

The RSV produced in accordance with the present disclosure can be combined with viruses of the other subgroup or strains to achieve protection against multiple RSV subgroups or strains, or protective epitopes of these strains can be engineered into one virus as described herein. Typically, the different viruses will be in admixture and administered simultaneously, but may also be administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

In some instances, it may be desirable to combine the RSV vaccines of the disclosure with vaccines which induce protective responses to other agents, particularly other childhood viruses. For example, the RSV vaccine of the present disclosure can be administered simultaneously with parainfluenza virus vaccine, such as described in Clements et al., J. Clin. Microbiol. 29:1175-1182 (1991), incorporated herein by reference. In another aspect of the disclosure the RSV can be employed as a vector for protective antigens of other respiratory tract pathogens, such as parainfluenza, by incorporating the sequences encoding those protective antigens into the RSV genome or antigenome which is used to produce infectious RSV as described herein.

Single or multiple administrations of the vaccine compositions of the disclosure can be carried out. In neonates and infants, multiple, sequential administrations may be required to elicit sufficient levels of immunity. Administration may begin within the first month of life, or before, about two months of age, typically not later than six months of age, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly (over 55, 60, or 65 years), or individuals with compromised cardiopulmonary function may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be advantageous for different recipient groups. For example, an engineered RSV strain expressing an additional protein rich in T cell epitopes may be particularly advantageous for adults rather than for infants.

In yet another aspect of the disclosure, RSV is employed as a vector for transient gene therapy of the respiratory tract. According to this embodiment, the recombinant RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2-1 proteins and containing a sequence encoding the gene product of interest is administered to a patient. Administration is typically by aerosol, nebulizer, or other topical application to the respiratory tract of the patient being treated. Recombinant RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

In certain embodiments, the disclosure relates to immunogenic compositions (e.g., vaccines) comprising an immunologically effective amount of a recombinant RSV of the invention (e.g., an attenuated live recombinant RSV or inactivated, non-replicating RSV), an immunologically effective amount of a polypeptide disclosed herein, and/or an immunologically effective amount of a nucleic acid disclosed herein.

In certain embodiments, the disclosure relates to methods for stimulating the immune system of an individual to produce a protective immune response against RSV. In the methods, an immunologically effective amount of a recombinant RSV disclosed herein, an immunologically effective amount of a polypeptide disclosed herein, and/or an immunologically effective amount of a nucleic acid disclosed herein is administered to the individual in a physiologically acceptable carrier.

Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions ensuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, oral, topical, etc. The resulting aqueous solutions can e.g., be packaged for use as is or lyophilized, the lyophilized preparation being combined with a sterile solution prior to administration In certain embodiments, the RSV (or RSV components) is administered in a quantity sufficient to stimulate an immune response specific for one or more strains of RSV (e.g., an immunologically effective amount of RSV or an RSV component is administered). Preferably, administration of RSV elicits a protective immune response. Dosages and methods for eliciting a protective anti-viral immune response, adaptable to producing a protective immune response against RSV, are known to those of skill in the art. See, e.g., U.S. Pat. No. 5,922,326; Wright et al. (1982) Infect. Immun. 37:397-400; Kim et al. (1973) Pediatrics 52:56-63; and Wright et al. (1976) J. Pediatr. 88:931-936. For example, virus can be provided in the range of about 103-106 pfu (plaque forming units) per dose administered (e.g., 104-105 pfu per dose administered). Typically, the dose will be adjusted based on, e.g., age, physical condition, body weight, sex, diet, mode and time of administration, and other clinical factors. The vaccine formulation can be systemically administered, e.g., by subcutaneous or intramuscular injection using a needle and syringe or a needleless injection device. Preferably, the vaccine formulation is administered intranasally, e.g., by drops, aerosol (e.g., large particle aerosol (greater than about 10 microns)), or spray into the upper respiratory tract. While any of the above routes of delivery results in a protective systemic immune response, intranasal administration confers the added benefit of eliciting mucosal immunity at the site of entry of the virus. For intranasal administration, attenuated live virus vaccines are often preferred, e.g., an attenuated, cold adapted and/or temperature sensitive recombinant RSV, e.g., a chimeric recombinant RSV. As an alternative or in addition to attenuated live virus vaccines, killed virus vaccines, nucleic acid vaccines, and/or polypeptide subunit vaccines, for example, can be used, as suggested by Walsh et al. (1987) J. Infect. Dis. 155:1198-1204 and Murphy et al. (1990) Vaccine 8:497-502.

In certain embodiments, the attenuated recombinant RSV is as used in a vaccine and is sufficiently attenuated such that symptoms of infection, or at least symptoms of serious infection, will not occur in most individuals immunized (or otherwise infected) with the attenuated RSV-in embodiments in which viral components (e.g., the nucleic acids or polypeptides herein) are used as vaccine or immunogenic components. However, virulence is typically sufficiently abrogated such that mild or severe lower respiratory tract infections do not typically occur in the vaccinated or incidental subject.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type RSV infection. Similarly, adults who are particularly susceptible to repeated or serious RSV infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of virus-neutralizing secretory and serum antibodies, and dosages adjusted or vaccinations repeated as necessary to elicit and maintain desired levels of protection.

Alternatively, an immune response can be stimulated by ex vivo or in vivo targeting of dendritic cells with virus. For example, proliferating dendritic cells are exposed to viruses in a sufficient amount and for a sufficient period of time to permit capture of the RSV antigens by the dendritic cells. The cells are then transferred into a subject to be vaccinated by standard intravenous transplantation methods.

Optionally, the formulation for administration of the RSV also contains one or more adjuvants for enhancing the immune response to the RSV antigens. Contemplated adjuvants include aluminum salts such as Alhydrogel® and Adjuphos®. Contemplated adjuvants include oil-in-water emulsions, where the oil acts as the solute in the water phase and forms isolated droplets, stabilized by emulsifying agents. In certain embodiments, emulsions contain a squalene or a-tocopherol (vitamin E) with additional emulsifying agents such as sorbitan trioleate and polysorbate-80 (PS80) as surfactants. In certain embodiments, emulsions contain a glucopyranosyl lipid A (GLA). GLA can be formulated with chimeric RSV, particles or RSV F protein either alone or in a squalene-based oil-in-water stable emulsion (SE). Iyer et al report oil-in-water adjuvants of different particle size using Respiratory Syncytial Virus Fusion protein (RSV-F). Hum Vaccin Immunother, 2015, 11 (7): 1853-1864

Suitable adjuvants include, for example: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvant QS-21.

If desired, prophylactic vaccine administration of RSV can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the RSV, or can be administered separately. Either the protein or an expression vector encoding the protein can be administered to produce an immunostimulatory effect.

Although vaccination of an individual with an attenuated RSV of a particular strain of a particular subgroup can induce cross-protection against RSV of different strains and/or subgroups, cross-protection can be enhanced, if desired, by vaccinating the individual with attenuated RSV from at least two strains, e.g., each of which represents a different subgroup. Similarly, the attenuated RSV vaccines can optionally be combined with vaccines that induce protective immune responses against other infectious agents.

Assembly and Rescue of Chimeric RSV Viruses

The following recombinant viruses: A2, A2-line19F, A2-line19F (M79I), A2-line19F (R191K), A2-line19F (K357T), A2-line19F (Y371N), A2-line19F (1557V), A2-line19F (K357T/Y371N), and A2-mKate2-2-20F/G, can be prepared as described in:

Hotard et al. Identification of residues in the human respiratory syncytial virus fusion protein that modulate fusion activity and pathogenesis. J Virol 89, 512-522 (2015).

Meng et al. Respiratory Syncytial Virus Attachment Glycoprotein Contribution to Infection Depends on the Specific Fusion Protein. Journal of virology 90, 245-253 (2015)

Hotard et al. A stabilized respiratory syncytial virus reverse genetics system amenable to recombination-mediated mutagenesis. *Virology* 434, 129-136 (2012).

The bacterial artificial chromosome (BAC) construct for OF4 was generated through modification of the published BAC containing A2-mKate2-line19F (1557V). The gene for monomeric Katushka 2 (mKate2, K), a far-red fluorescent reporter, is in the first gene position of the RSV antigenomic cDNA. Inclusion of mKate2 in this position did not attenuate RSV in vitro or in mice. Deletion of SH (ΔSH) was performed by recombination-mediated mutagenesis (recombineering). The following oligonucleotides (Integrated DNA Technologies/IDT) were used to PCR-amplify the galK cassette such that the amplicon termini are homologous to the target replace SH with galK: dSH50f

```
(SEQ ID NO: 5)
5'-AGATCTAGTACTCAAATAAGTTAATAAAAAATATACACATGGACGT
CCATCCTGTTGACAATTAATCATCGGCA-3'),
``` where the underlined portions represent the 50 nt immediately upstream of the SH gene start in the BAC, and dSH50r

```
(SEQ ID NO: 6)
5'-GTCTTAGCGGTGCGTTGGTCCTTGTTTTTGGACATGTTTGCATTTG
CCCCTCAGCACTGTCCTGCTCCTT-3'),
``` where the underlined portion represents the complement of 50 nt beginning with the G gene start in the BAC. The non-underlined portions of the primers are specific to the galK cassette, as described37. Recombination in *E. coli* resulted in replacing SH, from the beginning of the gene start to the end of the SH-G intergenic region, with the galK cassette. The following complementary oligonucleotides were annealed and used for removing the galK cassette in the second step of recombineering: dSH100f

```
(SEQ ID NO: 7)
5'-AGATCTAGTACTCAAATAAGTTAATAAAAAATATACACATGGACGT
CCATGGGGCAAATGCAAACATGTCCAAAAACAAGGACCAACGCACCGCT
AAGAC-3')
``` and dSH100r

```
(SEQ ID NO: 8)
5'-GTCTTAGCGGTGCGTTGGTCCTTGTTTTTGGACATGTTTGCATTTG
CCCCATGGACGTCCATGTGTATATTTTTATTAACTTATTTGAGTACTA
GATCT-3').
```

Precise deletion of SH was confirmed by sequencing, yielding A2-K-ΔSH-line19F (1557V) BAC.

The human codon-deoptimized NS1 and NS2 coding region (dNSh) was digested from the BAC used for recovery of A2-dNSh and ligated into the A2-K-ΔSH-line19F (1557V) BAC yielding an A2-K-dNSh-ΔSH-line19F (1557V). This construct was used for recovery of OE4+ wild-type A2 G (termed OE4+wtG). Codon-deoptimization of G was performed through substitution in silico of all codons least frequently used based on human codon usage bias into the RSV G sequence of A2. A point mutation (M481) was introduced to ablate the secreted form of G. The coding region of codon-deoptimized G (dG) was synthesized by GenScript and cloned by restriction digestion and ligation into the A2-K-dNSh-ΔSH-line 19F (1557V) BAC yielding A2-K-dNSh-ΔSH-dG-line19F (1557V) yielding the recovery BAC for OE4.

The BAC for rescue of BAF was generated by cloning the Buenos Aires consensus F (BAF) gene sequence into the OE4+wtG BAC through the methods described above. BAF-357/371 was generated through introduction of the Line19 F residues K357 and Y371 into the BAF coding sequence. The BAC for rescue of A2-ΔM2-2 was generated by recombineering. As had been done for ΔM2-238234 nt (from the 7th codon to the stop codon) of M2-2 were deleted. The following oligonucleotides were used to PRC-amplify the galK cassette for the first step of recombineering, delM2-1-f (SEQ ID NO: 9)
5'-TTAGTGATACAAATGACCATGCCAAAAATAATGATACTACCTGACAAATACCTGTTGACAATTAATCATCGGCA-3')

and delM2-2-r (SEQ ID NO: 10)
5'-ATTGTTTGAATTAATAATGTAACGATGTGGTGAGTGTTAGAATTGAGTGTTCAGCACTGTCCTGCTCCTT-3').

The following complementary oligonucleotides were annealed and used for the second recombineering step, M22_100f (SEQ ID NO: 11)
5'-TTAGTGATACAAATGACCATGCCAAAAATAATGATACTACCTGACAAATAACACTCAATTCTAACACTCACCACATCGTTACATTATTAATTCAAACAAT-3'), and M22_100r (SEQ ID NO: 12)
5'-ATTGTTTGAATTAATAATGTAACGATGTGGTGAGTGTTAGAATTGAGTGTTATTTGTCAGGTAGTATCATTATTTTTGGCATGGTCATTTGTATCACTAA-3').

Precise deletion of the targeted 234 nt was confirmed by sequencing.

Recombinant viruses were rescued in BSR-T7/5 cells, and virus stocks were propagated in Vero cells.

The panel of RSV strains used for quantification of RSV nAb titers in cotton rat anti-sera were generated by first having cDNAs of F and G genes of the following A and B strains synthesized (GeneArt, Invitrogen): RSVA/1998/12-21 (JX069802), Riyadh A/91/2009 (JF714706/JF714710); and RSV B strains NH1276 (JQ680988/JQ736678), 9320 (AY353550), and TX11-56 (JQ680989JQ736679). The G and F gene segments were cloned into the A2-K BAC by restriction digestion and ligation, and the reporter viruses were recovered by transfection into BSR-T7/5 cells, followed by propagation of stocks in HEp-2 cells.

Recombinant viruses were recovered by cotransfecting the RSV antigenomic BACs with four human codon-optimized helper plasmids that expressed RSV N, P, M2-1, or L protein into BSR T7/5 cells. Master and working virus stocks of vaccine strains were subsequently propagated and harvested in Vero cells.

Pre-F Antigen ELISA

Virus aliquots were thawed and diluted in MEM to yield high titer stock suspensions. 100 µL of each virus stock suspension was added to triplicate series of wells in a Costar Assay Plate, High Binding (Corning). The plates were covered and incubated at room temperature overnight. The next day, the virus suspension was dumped from the plate, and the plate was washed once with 150 uL per well of PBS-Tween (PBST, 0.05% Tween20 in PBS) followed by addition of 150 µL of 5% BSA (in PBS) per well for blocking. The plate was incubated at room temperature for 2 h. Pre-F-specific mAb MPE839 was generated by U-Protein Express in HEK293-X2FreeStyle cells using human codon-optimized VH and VL sequences. Motavizumab mAb which binds pre-F and post-F was provided by Nancy Ulbrandt (MedImmune/AZ). MPE8 and motavizumab antibodies were prepared by diluting the antibodies to 1 µg/mL in PBS before further dilution of 1:10,000 to 1:320,000 by serial dilutions in 1% BSA. Following blocking, the plate was washed once again with 150 µL per well of PBST before 100 µL of the diluted primary antibodies were applied to the wells. The plate was incubated for 2 h at room temperature before being dumped and washed three times with 150 uL per well of PBST. After washing, 100 µL of a 1:10,000 dilution of anti-human-HRP antibody in 1% BSA was applied and the plate incubated an hour at room temperature. Then the plate was dumped and washed 3 times with 150 µL of PBST before 100 µL of a pre-mixed reactive substrate reagent mixture (R&D Systems) was applied to catalyze a colorimetric reaction. The plate was covered and incubated for approximately 10 min before the reaction was quenched by the addition of 100 µL of 0.2N sulfuric acid. The plate was read at 450 nm on an ELISA plate reader. The absorbance readings collected were subtracted from background and plotted to a curve. The ratio of the area under the curve for MPE8 (pre-F) to the area under the curve for motavizumab (pre-F and post-F, total F) was used to determine pre-F level normalized to total F.

Growth in Vero

BEAS-2B, NHBE, and HAE cells. The media from 70% confluent Vero or BEAS-2B cells in 6-well plates was aspirated, and 0.5 mL of virus at an MOI of 0.01 was added to replicate wells for each of the time points to be acquired for each virus strain. The plates were rocked at room temperature for 1 h. Following infection, the virus was carefully aspirated and the monolayers washed twice with 1 mL of PBS before 2 mL of pre-warmed complete E-MEM (Vero) or RPMI (BEAS-2B) was added. The plates were incubated at 37° C. and 5% CO2 for the duration of the time courses. Time points were acquired at 1, 12, 24, 36, 48, 72, and 96 h post-infection. At each time point, the monolayers were scrapped into the supernatant, vortexed briefly, and flash frozen in liquid nitrogen before storage at −80° C. NHBE cells from two donors were differentiated at ALI and the monolayers washed with PBS before being infected apically with 100 µL of virus at an MOI of 2.6. The virus was left to incubate for 2 h at 37° C. before removal and 3 subsequent washes with PBS. At designated time points, 150 µL of differentiated medium without inducer was incubated on the apical surface for 10 min at 37° C. before harvesting and transfer into microcentrifuge tubes. The process was repeated to yield a total of 300 µL of pooled apical wash, which was frozen in liquid nitrogen and stored at −80° C. for later titration. Similar to the NHBE infection, HAE cells from two donors were differentiated at ALI, the apical surface washed with PBS, and infected with an initial MOI of 6.7. Following 2 hr incubation at 37° C., the virus inoculum was aspirated, the apical layer washed 3 times with PBS and the culture incubated at 37° C. For each designated time point, the apical layers were washed with 425 µL of media for 30 min at 37° C. and the supernatant stored at −80° C. FFU titration was performed for all analyses as described above on either HEp-2 or Vero cells.

Viral Load, Neutralization Titers, and Protection in Mice

For determination of viral load, 7-week-old female BALB/c mice (Charles River) were infected i.n. under sedation with 100 µL of virus in serum-free MEM. On days 2, 4, 6, and 8, the mice were euthanized and the left lung harvested for viral FFU titer assay. Titers below the limit of detection were assigned a value equal to half of the limit of detection. For determination of serum nAb titers and challenge studies, 7-week-old female BALB/c mice (Jackson) were infected i.n. with 100 µL of virus in serum-free MEM. On days 35, 70, and 100, the mice were sedated and serum samples obtained via submandibular vein bleeding. Sera were stored at −80° C. until quantification by a FFU microneutralization assay. Neutralization titers were determined by co-incubating heat-inactivated (56° C., 30 min) sera, which had been two-fold serially diluted with 50 –100 FFU of virus for 1 h at 37° C. The serum-virus mixtures were then spinoculated onto HEp-2 monolayers in 96-well plates at 2900×g for 30 min at 4° C. before being overlaid with 0.75% methylcellulose in complete MEM. FFU per well were counted 2 days later, and EC50 titers were determined by nonlinear regression analysis. To challenge the mice after vaccination, the mice were sedated on day 102 post-inoculation and infected i.n. with 105 PFU A2-line19F. After 4 days, the viral load was determined on the left lung by plaque assay on HEp-2 cells.

A Live-Attenuated RSV Vaccine with Enhanced Thermal Stability and Immunogenicity Like other paramyxovirus fusion proteins, RSV fusion glycoprotein (RSV F) is a type I integral membrane protein that mediates fusion of the viral envelope and target cell. RSV F initially assembles in the virion membrane as a trimer in a metastable, pre-fusion conformation. Triggering results in major refolding of F into a post-fusion form, which approximates viral and target membranes and mediates fusion. Since both pre-F and post-F are present on RSV virions in prepared virus stocks, the relative amount of pre-F antigen in RSV stocks using an ELISA-based approach was evaluated. Strain A2-line19F, which expresses the F protein of strain line 19 in the background of the prototypical A2 strain, exhibited significantly higher relative binding to a pre-F-specific mAb than strain A2. Intranasal (i.n.) inoculation of BALB/c mice with A2-line19F resulted in higher nAb titers than A2.

There are five amino acid residues unique to line 19 F: M79, R191, K357, Y371, and I557. Pre-F antigen ELISAs on A2-line19F mutants containing A2 residues at each of these positions showed that residues K357 and Y371 are important for line 19 F pre-F antigen levels.

RSV is known to be a heat-labile virus, and elevated temperatures can trigger transition to the RSV post-F conformation. RSV with enhanced pre-F levels should be more resistant to temperature-inactivation. RSV A2-line19F infectivity was more thermostable over time than A2 at 4° C. and 37° C., a phenotype mediated in part by the K357 and Y371 residues of line 19 F. K357 and Y371 were introduced into the F of a genetically divergent vaccine strain DB1, which expresses a consensus F gene of the antigenic subgroup B "Buenos Aires" (BAF) clade. We previously described the generation of DB1, which also contains codon-deoptimized non-structural protein genes and deleted SH gene, with a genotype RSV-A2-dNS1-dNS2-ΔSH-BAF. DB1 expressed low levels of pre-F antigen and was thermally unstable; however, incorporation of the K357 and Y371 residues to generate DB1-357/371 enhanced MPE8 binding and partially restored thermal stability. These data demonstrated that residues 357 and 371 governed not only MPE8 binding, a correlate of pre-F antigen levels, but also viral resistance to thermal inactivation in viral stocks.

An RSV LAV called OF4, was generated by incorporating line 19 F into a multi-component vaccine. The NS1 and NS2 genes, which encode two nonstructural proteins of RSV that suppress host innate immunity by targeting interferon pathways and suppressing apoptosis, were codon-deptimized. Codon-deoptimization of NS1 and NS2 genes was genetically stable and reduced NS1 and NS2 protein expression, resulting in virus attenuation with slightly enhanced immunogenicity in mice. The small hydrophobic (SH) protein gene was deleted with the goal of increasing the transcription of downstream viral genes, including F, by altering their proximity to the viral leader. The deletion of SH is also mildly attenuating in mice and chimpanzees, but conferred no apparent attenuation in a vaccine candidate in children in prior studies. The RSV attachment (G) glycoprotein gene was codon-deoptimized, and the secreted form of G was ablated by a point mutation. RSV expresses a membrane-bound form (Gm) and a secreted form (Gs) of G, which are not required for viral replication in immortalized cell lines. RSV G is capable of eliciting protective neutralizing antibodies. However, G is less conserved than F and suppresses the innate immune response through chemokine mimicry. Gs functions as an antigen decoy and can alter dendritic cell signaling and activation through interactions with C-type lectins. The resulting genotype of the OF4 vaccine candidate was RSV-A2-dNS1-dNS2-ΔSH-dG$_m$-Gs$_{null}$-line19F. Using Western blotting, it was determined that OE4 had decreased expression levels of NS1, NS2, and G compared to parental A2. OE4 had higher levels of F expression than A2-line19F, likely attributable to the deletion of SH.

MPE8 and D25 binding of OE was analyzed, and vaccine thermal stability at 4° C. and 37° C. was measured. Similar to A2-line19F, OE4 exhibited high relative pre-F antigen levels by antibody binding and thermal stability consistent with its expression of the line 19 F protein. Pre-F stability as measured was quantified by MPE8 binding of OE4 and A2 from virus stocks incubated at 4° C. over time. Relative pre-F antigen levels declined in both viruses over a period of 8 days. Therefore, the kinetics of thermal stability of A2 and OE4 infectivity did not correlate with the decay of pre-F antigen levels. However, OE4 maintained greater than twice the levels of pre-F antigen levels at each time point compared to A2, and a minimal threshold of pre-F may be sufficient to maintain infectivity.

In order to assess the overall structure of the virions and glycoprotein incorporation into RSV A2 and OE4, thin-section transmission electron microscopy (TEM), native immuno-TEM, and cryo-electron tomography (cryo-ET) of viruses budded from BEAS-2B cells was performed. BEAS-2B are an immortalized human bronchial epithelial cell line. Virus-infected cells and released virions were analyzed following minimal sample processing to maximize preservation of the native structure of the virions. First, native immunogold labeling combined with thin-section TEM was performed using mAbs which preferentially bound pre-F (MPE8), post-F (131-2A), total F (motavizumab), or G (131-2G). The density of gold particles per membrane length was quantified for each virus and immunolabel. (E4 virus particles exhibited a greater density of incorporated pre-F and total F than A2, potentially due to the deletion of SH. There was no significant difference in the amount of post-F detected on the surfaces of A2 and OF4 particles. G protein density on OF4 particles was significantly reduced, as was expected in the setting of codon-deoptimization of the G gene.

The OE4 vaccine candidate was characterized in vitro by measuring attenuation levels in immortalized cells and in primary human airway epithelial cells. In Vero cells, which were used for virus stock generation, OE4 grew to titers slightly below the parental un-attenuated A2-line 19F. OE4 was more attenuated relative to wild-type in BEAS-2B cells. We then evaluated OE4 growth in primary human airway epithelial cells, which are an established system for approximating RSV LAV attenuation in seronegative children. We implemented two models, NHBE-ALI and HAE-ALI, and found that OE4 was significantly attenuated in both models and exhibited deficiency in spreading through the cultures. The codon-deoptimization of G in OE4 contributed significantly to the level of attenuation compared to OE4 expressing wild-type G (OE4+wtG) in NHBE-ALI, likely due to the previously described attachment role of G in primary cells. In BALB/c mice, OE4 was moderately attenuated and elicited nAb titers equivalent to A2-line19F and higher than A2. Following i.n. inoculation, mice were challenged on day 102 with A2-line19F, and the OE4-vaccinated mice were completely protected against the challenge.

OE4 was evaluated in cotton rats prior to clinical testing. In cotton rats, OE4 was highly attenuated in the upper and lower respiratory tracts and OE4 induced relatively high levels of serum nAb against a panel of RSV strains representing RSV diversity. OE4-vaccinated cotton rats were completely protected against RSV challenge, not only in lungs but also in the upper respiratory tract. OE4 established effective mucosal immunity despite being highly attenuated.

A primary concern highlighted, by the failure of another RSV vaccine candidate, formalin-inactivated RSV, is the potential for vaccine-enhanced priming for disease upon natural infection. Although RSV LAV candidates have not been shown to cause enhanced illness, whether the novel vaccination strategy employed by OE4 results in priming for enhanced disease upon challenge was evaluated in cotton rats. RSV challenge did not result in enhanced illness following infection with OE4 compared to mock. In contrast, formalin-inactivated RSV did result in enhanced disease associated with elevated peribronchiolar infiltration and alveolitis compared to OE4 and mock.

A Chimeric Respiratory Syncytial Virus Vaccine Candidate Attenuated by a Low-Fusion F Protein is Immunogenic and Protective Against Challenge in Cotton Rats The Buenos Aires F protein (BAF), when expressed alone, was poorly fusogenic compared to A2F and line19F proteins. Reverse genetics were implemented to design a LAV that combined the codon deoptimization of genes for non-structural proteins NS1 and NS2 (dNS); deletion of the small hydrophobic protein (ΔSH) gene; and replacement of the wild-type fusion (F) protein gene with a low-fusion RSV subgroup B F consensus sequence of the Buenos Aires clade (BAF). This vaccine candidate RSV-A2-dNS-ΔSH-BAF named "DB1" was attenuated in two models of primary human airway epithelial cells and in the upper and lower airways of cotton rats. DB1 was also highly immunogenic in cotton rats and elicited broadly neutralizing antibodies against a diverse panel of recombinant RSV strains. When vaccinated cotton rats were challenged with wild-type RSV A, DB1 reduced viral titers in the upper and lower airways by 3.8 $\log_{10}$ total PFU and 2.7 $\log_{10}$ PFU/g tissue respectively compared to unvaccinated animals ($P<0.0001$). DB1 was thus attenuated, highly immunogenic, and protective against RSV challenge in cotton rats. DB1 is the first RSV LAV to incorporate a low-fusion F protein as a strategy to attenuate viral replication and preserve immunogenicity.

DB1 was greater than 10-fold attenuated in cotton rat upper and lower airways, yet still elicited high titers of broadly nAb to a diverse panel of RSV A and B recombinant strains. DB1 also generated mucosal immunity in the form of RSV-specific IgA antibodies in cotton rat nasal wash specimens. When vaccinated animals were challenged with RSV, DB1 reduced challenge strain titers by >99% in both the nasal wash and lung lavage specimens. Thus, DB 1 was attenuated, highly immunogenic, and efficacious at protecting against RSV challenge in cotton rats.

The invention claimed is:

1. A respiratory syncytial virus (RSV) F protein comprising K at position 357 and Y at position 371, each relative to amino acid sequence as set forth in SEQ ID NO: 4, provided that the RSV F protein has less than 98% sequence identity to SEQ ID NO: 4; and wherein the RSV F protein has more than 90% sequence identity to SEQ ID NO: 1.

2. The RSV F protein of claim 1, further comprising M at position 79, R at position 191, and/or V at position 557.

3. The RSV F protein of claim 1, wherein the RSV F protein has more than 95% sequence identity to SEQ ID NO: 1.

4. The RSV F protein of claim 1, wherein the RSV F protein comprises SEQ ID NO: 1.

5. The RSV F protein of claim 1, wherein the RSV F protein is derived from an RSV strain of subgroup B.

6. The RSV F protein of claim 1, wherein the RSV protein is derived from the Buenos Aires clade.

7. The RSV F protein of claim 1, wherein the F protein is mutated such that position 557 is not V.

8. The RSV F protein of claim 7, wherein the F protein is mutated such that I is in position 557.

9. A respiratory syncytial virus (RSV) F protein comprising K at position 357 and Y at position 371, each relative to amino acid sequence as set forth in SEQ ID NO: 4, provided that the RSV F protein has less than 98% sequence identity to SEQ ID NO: 4; and wherein the RSV F protein has more than 90% sequence identity to SEQ ID NO: 13.

10. The RSV F protein of claim 9, further comprising M at position 79, R at position 191, and V at position 557.

11. The RSV F protein of claim 9, wherein the RSV F protein has more than 95% sequence identity to SEQ ID NO: 13.

12. The RSV F protein of claim 9, wherein the RSV F protein comprises SEQ ID NO: 13.

13. The RSV F protein of claim 9, wherein the RSV F protein is derived from an RSV strain of subgroup B.

14. The RSV F protein of claim 9, wherein the RSV protein is derived from the Buenos Aires clade.

15. The RSV F protein of claim 9, wherein the F protein is mutated such that position 557 is not V.

16. The RSV F protein of claim 9, wherein the F protein is mutated such that I is in position 557.

* * * * *